(12) United States Patent
Henry et al.

(10) Patent No.: US 8,895,555 B2
(45) Date of Patent: Nov. 25, 2014

(54) METHODS OF TREATING INTESTINAL DISEASES AND INFLAMMATORY CONDITIONS RELATED TO HIV-AIDS

(75) Inventors: Mark O. Henry, North Andover, MA (US); William S. Lynn, Hillsborough, NC (US)

(73) Assignee: Bach Pharma, Inc., North Andover, MA (US)

( * ) Notice: Subject to any disclaimer, the term of this patent is extended or adjusted under 35 U.S.C. 154(b) by 932 days.

(21) Appl. No.: 12/709,108

(22) Filed: Feb. 19, 2010

(65) Prior Publication Data

US 2010/0255077 A1 Oct. 7, 2010

Related U.S. Application Data

(60) Provisional application No. 61/153,904, filed on Feb. 19, 2009, provisional application No. 61/153,905, filed on Feb. 19, 2009.

(51) Int. Cl.
*A61K 31/502* (2006.01)
*A61K 45/06* (2006.01)

(52) U.S. Cl.
CPC .............. *A61K 31/502* (2013.01); *A61K 45/06* (2013.01)
USPC .......................................... 514/248; 514/247

(58) Field of Classification Search
None
See application file for complete search history.

(56) References Cited

U.S. PATENT DOCUMENTS

| | | | |
|---|---|---|---|
| 5,543,410 A | 8/1996 | Minin et al. | |
| 6,444,676 B1 * | 9/2002 | Pang et al. | 514/253.02 |
| 6,953,799 B1 | 10/2005 | Henry et al. | |
| 7,326,690 B2 | 2/2008 | Henry et al. | |
| 7,691,819 B2 | 4/2010 | Henry et al. | |
| 2005/0009772 A1 | 1/2005 | Caprioli et al. | |
| 2005/0288291 A1 | 12/2005 | Henry et al. | |
| 2007/0142303 A1 | 6/2007 | Henry et al. | |
| 2009/0036411 A1 | 2/2009 | Henry et al. | |
| 2010/0086531 A1 | 4/2010 | Henry et al. | |
| 2010/0222584 A1 | 9/2010 | Henry et al. | |

FOREIGN PATENT DOCUMENTS

EP 0617024 B1 7/1999

OTHER PUBLICATIONS

"Extraintestinal manifestations in inflammatory bowel disease" by Danese et al., World J. Gastroenterol. 11, 7227-36 (2005).*
CAS Registry Record for Luminol (retrieved Jan. 2013).*
"Human immunodeficiency virus infection, the acquired immunodeficiency syndrome, and inflammatory bowel disease" by Yoshida et al., J. Clin. Gastroenterol. 23, 24-28 (PubMed Abstract No. 8835895) (1996).*
"The Role of Inflammation in the Pathogenesis of Glaucoma" by Vohra et al., Surv. Ophthalmol. 58, 311-20 (2013).*
Jiang et al., Retrovirus-Induced Oxidative Stress with Neuroimmunodegeneration is Suppressed by Antioxidant Treatment with a Refined Monosodium ($_\chi$-Luminol (Galavit); *J.Virol.*, 80(9);4557-4569 (2006).
Scofield et al., "The drug monosodium luminol (GVT) preserves crypt-villus epithelial organization and allows survival of intestinal T cells in mice infected with the *ts retrovirus*", Immunology Letters, vol. 122, pp. 150-158 (2009).
Mintz, et al., "Ocular Manifestations of Inflammatory Bowel Diseases," Inflammatory Bowel Diseases, vol. 10, Issue 2, pp. 135-139, Mar. 2004.

* cited by examiner

*Primary Examiner* — Theodore R West
(74) *Attorney, Agent, or Firm* — McCarter & English LLP; Elizabeth A. Hanley; Michael J. DeGrazia

(57) ABSTRACT

Provided herein are methods of treating intestinal diseases or inflammatory conditions, including HIV-AIDS, in which oxidative stress is a triggering or exacerbating factor by administering GVT to a patient suffering from the condition such that the condition is treated.

13 Claims, 16 Drawing Sheets

METHODS OF TREATING INTESTINAL DISEASES AND INFLAMMATORY CONDITIONS RELATED TO HIV-AIDS

RELATED APPLICATIONS

This application is entitled to the benefit of earlier filed U.S. Provisional Patent Application Ser. No. 61/153,904 filed on Feb. 19, 2009, and U.S. Provisional Patent Application No. 61/153,905 filed on Feb. 19, 2009 under 35 U.S.C. §119(e), the entire disclosures of which are hereby incorporated by reference herein.

BACKGROUND

In healthy cells, a balance of redox reactions maintains a physiologically appropriate environment for various cellular functions related to growth, differentiation, activity, and death. The proper coordination of such functions ensures homeostasis and the health of cells. Research has shown that alterations in cellular redox status affect activities such as cellular signaling, suggesting that altering the cellular redox status could also affect cellular activation, which results from certain cellular signals (U.S. Pat. No. 5,994,402). Altering the intracellular redox state by depleting cells of glutathione (GSH), an endogenous "redox agent," has also been shown to protect cells from certain injury and to promote their survival (U.S. Pat. No. 5,994,402), again suggesting a link between alterations in the cellular redox state and cellular functions.

An imbalanced redox state, even if not the cause of a particular disease condition, may facilitate that condition by providing an "unhealthy" environment in which necessary cellular functions become impaired. Cellular redox status may become impaired in numerous disease conditions. Under the stress of a disease state, the rate of redox reactions increases or decreases as needed by the cell. Significant or prolonged deviations in the intracellular redox status disable cellular processes, including defense mechanisms. When such cellular functions are impaired, the survival of the cell becomes uncertain. Maintenance of the proper redox status is thus critical to the fate of the cell.

To counter and correct disturbances in the redox status, cells require agents that can modulate redox imbalances, to facilitate reduction or oxidation reactions as appropriate. Agents currently available for correcting redox imbalances are inadequate in that they are labile, quickly oxidized, or unable to translocate to the proper region of the cell. Examples of such exogenous redox agents include cysteine, reduced lipoates or thiols, glucocorticoids, and other antioxidants. Redox agents that remain stable, active, and functional in the cellular environment are necessary.

Phthalazinediones and phthalazinedione derivatives have been described as effective against certain conditions associated with redox imbalances such as inflammation, cancer, arrhythmia, hyperlipidemia, and hypoxia (U.S. Pat. Nos. 6,686,347; 6,489,326; 5,874,444; 5,543,410; 5,512,573; 4,861,778; 4,250,180; Hall et al., Biomed. Biochim. Acta. Al: 423-433 (1988); Hall et al., J Pharm. Pharmacol. 41: 394-397 (1989); Hall et al., Anticancer Drugs. 3: 55-62 (1992); Burner et al., Int. J. Tissue React. 18: 47-55 (1996)). However, toxicity and the lack of pharmacological activity of certain phthalazinediones, including 2,3-dihydrophthalazine-1,4-dione and 5-amino-2,3-dihydrophthalazine-1,4-dione, were also noted (U.S. Pat. Nos. 6,489,326; 5,543,410; 5,512,573).

It has been demonstrated that certain intestinal diseases and intestinal inflammatory conditions are related to HIV-AIDS. Particularly, it has been demonstrated that these diseases and inflammatory condition are due, at least in part, to the accumulation of reactive oxygen species and oxidative stress.

SUMMARY

The present invention provides methods, uses, products and compositions for the treatment of diseases and inflammatory conditions of the intestinal environment that are due to HIV-AIDS. Phthalazinediones suitable for the methods herein disclosed are described herein and in U.S. patent application Ser. No. 12/701,088 filed on Feb. 5, 2010 and U.S. patent application Ser. No. 12/025,193 filed on Feb. 4, 2008, and U.S. Pat. No. 7,326,690 filed on Aug. 8, 2005 and U.S. Pat. No. 6,953,799 filed on Oct. 30, 2002; all of which are herein incorporated by reference in their entirety.

In certain non-limiting embodiments of the disclosed invention, methods are provided for the treatment of intestinal diseases that are related to oxidative stress in subjects suffering from HIV-AIDS. In certain embodiments of the methods, a therapeutically effective amount of a phthalazinedione is administered to a subject having an intestinal environment with an imbalanced redox state such that the oxidative stress related to the intestinal disease is modulated. The imbalance redox state is returned to a state of homeostasis upon administration of the phthalazinedione.

In certain embodiments of the methods, uses and products, the phthalazinedione is a purified form as recited in U.S. patent application Ser. No. 12/701,088 filed on Feb. 5, 2010, the disclosure of which is hereby incorporated by reference herein in its entirety. In some embodiments, the phthalazinedione is in a therapeutically effective form selected from the group including tablet, capsule, granule, powder, solution suspension, microsphere, liposome, colloid, spray and suppository. The phthalazinedione is administered by a means selected from the group including intravenous, intramuscular, intraperitoneal, subcutaneous, oral, nasal, mucosal, transdermal, parenteral, vaginal, and rectal in some embodiments. In some embodiments, the phthalazinedione is also administered as a combination treatment with other standard therapies such as surgery, drug therapy, and nutrition.

In certain embodiments of the methods, uses and products, the phthalazinedione is administered as a combination treatment with a compound selected from a group including a glutathione, cysteine, lipoic acid, biopterin, hydralazine, rasagiline, thioredoxin, ferulic acid, minocycline, menadione, tetracycline, isosorbate dinitrate, dextromethorphan, dithiothreitol, carnosine, and clomethiazole, wherein the metabolic distress is not caused by a disease of cellular senescence.

In certain embodiments of the methods, uses and products, the phthalazinedione is substituted by a substitutent selected from a group including haloamino, alkylamino, acylamino, alkanoamino, alkenylamino, alkoxyamino, haloalkylamino, allylamino, and sulfhydrylamino group. In some embodiments, the phthalazinedione is substituted by a substitutent selected from a group including a bromoamino, chloroamino, fluoroamino, iodoamino, methylamino, ethylamino, propylamino, isopropylamino, methanoylamino, ethanoylamino, propanoylamino, hydroxylamino, carboxylamino, methanolamino, ethenylamino, propenylamino, methoxyamino, ethoxyamino, propoxyamino, and dimethylamino group. In some embodiments, the phthalazinedione is at least one of 5-amino-2,3-dihydrophthalazine-1,4-dion-8-yl, 6-amino-2,3-dihydrophthalazine-1,4-dione, 5-amino-2,3-dihydrophthalazine-1,4-dione, N-bromo-5-amino-2,3-dihydrophthalazine-1,4-dione, N-chloro-5-amino-2,3- dihydrophthalazine-1,4-dione, N-fluoro-5-amino-2,3-dihydrophthalazine-1,4-dione, N-iodo-5-amino-2,3-dihydrophthalazine-1,4-dione, N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydrophthalazine-1,4-dione, N-ethanoyl-5-amino-2,3-dihydrophthalazine-1,4-dione, N-propanoyl-5-amino-2,3-dihydrophthalazine-1,4-dione, N-hydroxyl-5-amino-2,3-dihydrophthalazine-1,4-dione, N-carboxyl-5-amino-2,3-dihydrophthalazine-1,4-dione, N-methanol-5-amino-2,3-dihydrophthalazine-1,4-dione, N-ethanol-5-amino-2,3-dihydrophthalazine-1,4-dione, N-propanol-5-amino-2,3-dihydrophthalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydrophthalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5-amino-2,3-dihydrophthalazine-1,4-dione, N-acetylcysteine-5-amino-2,3-dihydrophthalazine-1,4-dione, and N-acetylglutathione-5-amino-2,3-dihydrophthalazine-1,4-dione.

In some embodiments of the methods, uses and products, the phthalazinedione is administered in an amount of about 0.01 mg/kg to about 100.0 mg/kg of body weight. In other embodiments, the phthalazinedione is administered in an amount of about 1.0 mg per day to about 10,000.0 mg per day.

In certain embodiments of the invention, the phthalazinedione is administered with a compound selected from a group including a glutathione, cysteine, lipoic acid, biopterin, hydralazine, rasagiline, thioredoxin, ferulic acid, minocycline, menadione, tetracycline, isosorbate dinitrate, dextromethorphan, dithiothreitol, carnosine, and clomethiazole, wherein the metabolic distress is not caused by a disease of cellular senescence.

In certain embodiments of the methods, uses and products, the administration of the phthalazinedione modulates the oxidative stress so as to prevent the oxidative stress from causing additional malfunctions in other organs remote from the intestinal environment. For example, in certain embodiments the oxidative stress in the intestinal environment may also manifest itself to cause inflammation or oxidative stress in the eye, resulting in glaucoma. In certain embodiments, the present invention provides methods for the treatment of glaucoma by the administration of a phthalazinedione to a subject such that the oxidative stress in the intestinal environment and in remote organs such as the eye are modulated. In certain embodiments of the methods, the modulation of the oxidative stress prevents diseases caused by oxidative stress originating in the intestinal environment. In certain embodiments the disease is glaucoma.

In certain embodiments of the methods, uses and products, the disease related to the oxidative stress in the intestinal environment is selected from a group including ocular inflammation, retinitis, protein misfolding, intestinal spirochetosis, *helicobacter pylori* infection, gastrointestinal immune system malfunction, gastroduodenal infection, dyspepsia, fungal infection, bacterial infection, parasite infection and a combination thereof. In certain embodiments, the ocular inflammation is related to glaucoma.

In certain other embodiments of the invention, methods are provided for the treatment of intestinal inflammation related to oxidative stress in a subject infected with HIV-AIDS. In certain embodiments of the methods, the intestinal inflammation is treated by administering a therapeutically effective amount of a phthalazinedione to the subject having an HIV-AIDS related inflammatory response, such that the inflammation is modulated.

In certain embodiments of the inventions, a phthalazinedione is used in the preparation of a medicament for the treatment of intestinal diseases related to oxidative stress in a subject infected with HIV-AIDS, wherein a therapeutically effective amount of a phthalazinedione is administered to the subject having an intestinal environment with an imbalanced redox state such that the oxidative stress related to the intestinal disease is modulated.

In certain embodiments of the methods, uses and products, the phthalazinedione is in the form of a tablet, capsule, granule, powder, solution, suspension, microsphere, liposome, colloid, lyophilized composition, gel, lotion, ointment, cream, spray or suppository. In certain embodiments the phthalazinedione is in the form of an eye drop solution.

In certain embodiments of the invention, a product is provided for the treatment of intestinal diseases related to oxidative stress in a subject infected with HIV-AIDS, wherein a therapeutically effective amount of a phthalazinedione is delivered upon administration to the subject having an intestinal environment with an imbalanced redox state such that the oxidative stress related to the intestinal disease is modulated. In other embodiments, a product is provided for the treatment of inflammation related to oxidative stress in a subject infected with HIV-AIDS, wherein a therapeutically effective amount of a phthalazinedione is delivered upon administration to the subject having an intestinal environment with an imbalanced redox state such that the oxidative stress related to the intestinal disease is modulated.

DETAILED DESCRIPTION

Definitions

Figure 1:
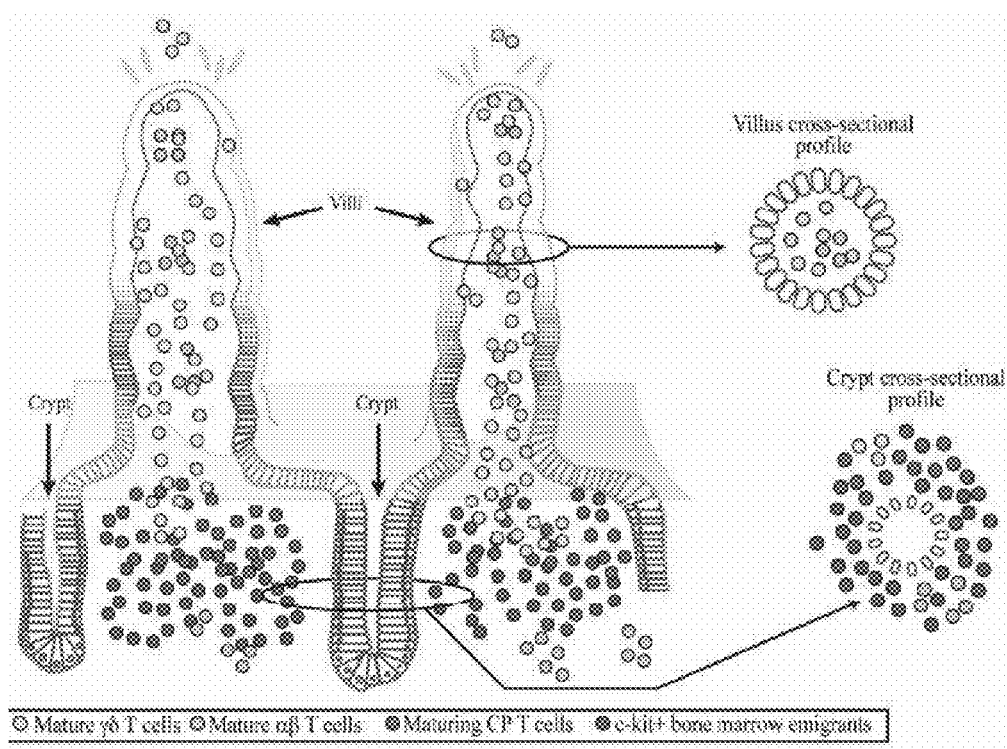
FIG. 1 is Diagram showing cell types and cytoarchitecture of the normal mouse small intestine.

In order to further clarify the disclosed embodiments of the invention, the following definitions are provided.

As used herein, "intestinal environment" refers to all portions of the small or large intestines including the esophagus, stomach, duodenum, small bowel, jejunum, Ileum, cecum, ascending colon, transverse colon, large bowel, descending colon, rectum and anus.

As used herein, "modulate", "modulated", or "modulation" refers to the act of bringing an imbalanced state to a state of substantial homeostasis.

As used herein, "therapeutically effective amount" refers to an amount of the active ingredient that is effective for achieving the desired treatment and may be determined by conventional methods known to those of ordinary skill in the art and may be affected by factors such as severity of conditions, number of malconditions, or subject.

As used herein "GVT" refers to a particular phthalazinedione manufactured by Bach Pharma, Inc. as monosodium luminol.

Description

The systemic consequences of ts1 infection are similar to HIV-AIDS in many respects as demonstrated by Wong P K, et al., *Ts1, a mutant of Moloney murine leukemia virus-TB, causes both immunodeficiency and neurologic disorders in BALB/c mice*, Virology 1989 and Clark S, et al., *ts1 and LP-BM5: a comparison of two murine retrovirus models for HIV*, Viral Immunology, 2001, 14:95-109 both of which are incorporated by reference herein in their entirety. Specific effects of ts1 infection on the mouse intestine are identified, whose symptomotology is similar to that induced by HIV-1, the primate retrovirus SHIV, and the feline immunodeficiency virus FIV. The intestinal epithelium can receive bone marrow T-cell progenitors and host their maturation into mature T cells. This aspect of intestine biology makes this tissue a likely first target for retroviral infection and cellular damage, especially since its T cell differentiation activities make it functionally equivalent to the thymus.

The present invention provides methods of treating a subject infected with ts1 or HIV-AIDS that include administering a phthalazinedione to the subject such that crypt-villus organization and T cell numbers remain normal and particularly such that reactive oxygen species that accumulate due to ts1 or HIV-AIDS infection are reduced and homeostasis is achieved. The examples herein demonstrate that crypt-villus organization and T cell numbers in ts1-infected mice are abnormal in ts1-infected mice having human cells, and that treatment of ts1-infected mice with a phthalazinedione prevents the abnormal T cell numbers.

In the exemplification, the serum thyrotropin (TSH) gradient of the crypt-villus axis of the intestines is shown to be lost in subjects infected with ts1. Treatment of ts1-infected subjects with A phthalazinedione have been demonstrated to prevent the loss of TSH gradient of the crypt villus axis of the intestine. Accordingly, in some embodiments, methods are provided wherein a subject infected with ts1 or HIV-AIDS is administered an effective amount of A phthalazinedione, and wherein loss of the TSH gradient of the crypt-villus axis of the intestines is prevented.

In the exemplification, the distinct cell cycling patterns of the crypt and villus are lost in subjects infected with ts1. The present invention provides methods of preventing the loss of the distinct cell cycling patterns of the crypt and villus that include administering GVT to the subject suffering from a ts1 or HIV-AIDS infection. In some embodiments, methods are provided wherein a subject infected with HIV-AIDS is such that loss of the distinct cell cycling patterns of the crypt and villus of the infected subject is prevented.

In some embodiments, methods are provided wherein a subject infected with ts1 or HIV-AIDS is treated such that intestinal epithelial cells contain high levels of the antioxidant transcription factor Nrf2, and the subject's T cells are protected from apoptosis. In some embodiments, methods are provided wherein a subject infected with HIV-AIDS is treated such that intestinal epithelial cells contain high levels of the antioxidant transcription factor Nrf2, and the subject's T cells are protected from apoptosis.

In some embodiments, methods are provided wherein a subject infected with ts1 or HIV-AIDS is treated such that accumulation of $gPr80^{env}$ is reduced. In further embodiments, methods are provided where a subject infected with HIV-AIDS is treated such that accumulation of $gPr80^{env}$ is reduced.

These methods may include additional treatments prior to, subsequent to, and/or concurrently with the administration of GVT. For example, in some embodiments, methods are provided wherein a subject infected with HIV-AIDS is treated with GVT in combination with HAART therapy such that any of the above conditions are treated. In some embodiments accumulation of gPr80env is reduced. In some embodiments, intestinal epithelial cells contain high levels of the antioxidant transcription factor Nrf2, and the subject's T cells are protected from apoptosis. In some embodiments, loss of the distinct cell cycling patterns of the crypt and villus of the infected subject is prevented. In some embodiments, loss of the TSH gradient of the crypt-villus axis of the intestines is prevented. In some embodiments, crypt-villus organization and T cell numbers remain normal.

The murine retrovirus MoMuLV causes thymic leukemias by 8-10 months of age in susceptible mice that are infected at birth. A mutant of MoMuLV, called ts1, causes a fulminant disease with a much shorter timecourse, leading to death of infected animals by 30 days after infection (dpi) if the mice are infected at birth. The ts1 mutant has a mutation in its env gene, so that productively infected cells contain an abnormal $gPr80^{env}$ preprotein. This abnormality interferes with the normal cleavage (as well as other cell processes) of the $gPr80^{env}$ to the mature viral envelope proteins gp70 and PrP15E. Without efficient cleavage, $gPr80^{env}$ accumulates in certain infected target cells and causes oxidative stress, including astrocytes in the central nervous system (CNS), thymocytes and T cells. In glial cells of the central nervous system, this accumulation initiates an unfolded protein response, endoplasmic reticulum stress, mitochondrial stress, oxidative stress and apoptosis. Similar responses occur in T-lineage cells of infected mice, which accumulate $gPr80^{env}$ and die as a consequence of oxidative stress-induced apoptosis, while blood vessel endothelial cells are infected but do not accumulate gPr80$^{env}$ and do not die.

FIG. 1 shows that mouse small intestines are composed of finger-like villi facing the gut lumen (top bracket), and of crypts buried in the mucosal connective tissue (bottom bracket). Both regions are covered with a continuous layer of epithelium, with the pluripotent stem cells for the entire epithelium residing in the lower crypts. These stem cells give rise to several cell types found on the villi: to absorptive enterocytes covering the villi (the predominant cell type in the mucosa), to mucus-producing goblet cells and enteroendocrine cells scattered over the villi between the enterocytes (specific cell types are not shown in the figure). These same crypt stem cells also give rise to defensin-producing Paneth cells, which form a cup at the bottom of the crypts, and which do not move upward toward the villi.

The progeny of the crypt epithelial stem cells are transit amplifying cells and differentiating cells, which move upward, as they divide, toward the CVJ. Once differentiated, these cells stop dividing, so that the epithelium covering the villi, above the CVJ, contains mostly quiescent enterocytes, goblet cells and enteroendocrine cells nudging each other passively upward to the tips of the villi. When the IECs arrive at the tips of the villi, they undergo apoptosis and are shed, together with any T cells that have inserted themselves between the cells (top of FIG. 1). The CVJ thus is a sharp boundary that separates dividing from quiescent cells.

Like the thymus, the small and large intestines of mammals can host the differentiation of bone marrow T-precursor cells into mature T cells. Recent laser-capture confocal microscopy studies established clonal identity between early T cell progenitors in CPs and mature T cells in the distal villi.

In addition to epithelial cells, FIG. 1 shows T-cell progenitors differentiating in the LP connective tissue beneath the CMJ, and mature T cells and above it. This reflects the continuous arrival in the crypts of bone marrow stem cells, which are c-kit-positive (red). These begin differentiation to become mitotic T-cell progenitor progeny in the crypt LP (purple). The maturing and fully mature descendants of these intestine-born T cells are CD8-positive T cells that reside in the LP of the villi. CD4+ cells are also present, but these arrive from the blood as mature T cells that have already completed their differentiation in the thymus. These are scattered throughout the crypt and villus LP. As in the thymus, therefore, the CVJ boundary separates distinct epithelia whose adjacent T cells are at distinct developmental stages.

In the normal thymus, the cortical and medullary epithelial cells express epithelial cells two distinct cytokeratin types. Unlike the thymus however, the intestinal epithelium is a simple epithelium throughout; and all of its cells express CK8 only, as do cortical epithelial cells of the thymus. However, two other differences distinguish the epithelial cells of the intestinal crypts from those of the villi. One of these is the constitutive expression of the thyroid stimulating hormone (TSH) by crypt epithelial cells, and not by epithelial cells of the villi. The other is the presence of dividing epithelial cells exclusively in crypts, but not in the villi. The presence and maintenance of these two standing gradients in the epithelial intestine reflects the presence of normally differentiating T-cell progenitors in the LP beneath, just as the presence of a healthy corticomedullary epithelial separation does for thymocytes. Like thymocytes, intestinal T cells undergo sequential developmental checkpoints that depend upon their being at the right place, at the right time, in relation to the epithelium above.

In mice infected with ts1 (ts1-only), it is demonstrated that intestinal epithelial cell gradients are dysregulated, that extensive T cell apoptosis occurs, and that the intestines collapse by 30 dpi. In mice infected with ts1 and also treated with GVT (ts1 GVT), however, the crypt-villus cytoarchitecture is intact at 30 dpi, intestinal epithelial cell gradients are in place, no T cell apoptosis is occurring, and the gPr80$^{env}$ protein is not accumulated by any cell type in the tissue. In the intact small intestines of GVT protected mice, most epithelial cells are negative for gp70, and thus do not appear to be infected, but they do contain large amounts of the transcription factor Nrf2, which orchestrates protective antioxidant responses. These effects of ts1-GVT treatment are remarkably similar to those occurring in the thymi of ts1-GVT mice, whose epithelial cells also become loaded with Nrf2.

Phthalazinediones may be used to control cell fates and act by serving as a redox buffer for the redox- and thiol-sensitive energy producing pathways in the mitochondrion, signaling pathways at the cell plasma membrane, and glutamate uptake and cytokine secretion by astrocytes in the central nervous system (see Trotti et al., J. Biol. Chem. 271: 5976-5979, 1996). In addition, amino phthalazinediones catalyze disulfide cross-linkages in the adenine nucleotide translocase (ANT) of the mitochondrial anion channels and in the megapores, which prevents energy production, increases reduction of the potent signal transducers hydrogen peroxide ($H_2O_2$) and superoxide (O2-) (see Zamzami et al., Oncogene 16: 1055-1063, 1998; Constantini et al., J. Biol. Chem. 271: 6746-6751, 1996), and liberates the apoptosis-inducing factors cytochrome c and AIF.

Under any stress, redox status is inevitably impaired as aerobic metabolism is necessarily overworked. Any stress to the cell, especially if prolonged, will deplete the cell of redox agents, including thiols, glutathione, thioredoxins, iron-sulfur proteins, cysteine, and thiol proteins, as well as redox-sensitive proteins such as catalase. Chronic stress leads to cellular and organelle thiol deficiencies, as blood cysteine is very limited. In turn, since many cellular pathways are controlled by or depend on intracellular redox activities, thiol deficiencies lead rapidly to impaired energy production, with increased oxidant production and progressive mitochondrial and cell death.

In tissue culture, small doses of less than 1 μg/ml of amino phthalazinediones are effective for conditions with chronic losses of cells, especially of stem or developing cells, as in neuroimmuno-degenerative syndromes, intestinal diseases or inflammation associated with HIV infection. In conditions where proliferation and apoptotic rates are out of control, including cancer, autoimmunity, infection, and traumas, in tissue culture, doses greater than 50 μg/ml of amino phthalazinediones are required. Successful treatment with the phthalazinedione compounds of the invention therefore depends both on redox diagnosis with repeated assessment of cellular thiol redox status and on maintenance of proper dosage of the compound over time. Treatment with phthalazinediones is directed at cells or organs such as the intestinal environment or remote organs affected by the inflammation or oxidative stress in the intestinal environment. In these cases, stress has dysregulated thiol redox homeostasis, with energy deprivation and oxidant stress.

In a preferred embodiment of the invention, amino phthalazinediones also act as efficient substrates for reaction with many of the reactive oxygen species and radicals that are inevitably generated in the stressed mitochondria in HIV infected subjects. The reactive oxygen species build up in the intestinal environments and are in some cases transported to other organs such as the eye where it facilitates the development of glaucoma. Because of antioxidant, redox-buffering, anti-inflammatory, antiproliferative, non-toxic, and immunomodulatory properties, phthalazinediones are beneficial as adjunctive support therapy for the stressed cell regardless of the compromising stress or its downstream symptoms. In rare disease states, redox support may be sufficient for the diseased cell to cure itself, but in some situations, the cell will also need the mechanical, pharmacological, or genetic support of conventional medical and nutritional therapies. The therapeutic methods of this invention should thus be used in combination with standard therapies for treating particular disease conditions.

In inflammatory conditions, such as acute infections, wounds, and immune responses, phthalazinediones, especially amino phthalazinediones, quickly ameliorate the painful redox-induced edematous swelling and facilitate rapid healing. Edematous inflammatory lesions in intestines, such as duodenal ulcers, ulcerative colitis, and acute vascular injury caused by HIV-AIDS infection, are all suppressed to some degree by thiol redox modulators, including dihydrolipoates, reduced biopterins, amino phthalazinedione, and more slowly by glucocorticoids. Healing rates increase, with replacement of the injured epithelial cells by redox-stimulated new cell growth. Thus, phthalazinedione, acting as redox modulators, suppress injurious over-reactive inflammatory responses and also facilitate healing and replacement of injured cells.

Oncogenic retroviral infections such as HIV in humans or MOMU-LV-Ts1 in mice cause degenerative cell changes in intestinal environment. Other cells like astrocytes and microglia in the intestinal environment become activated, secrete nitric oxide (NO) and superoxide ($O_2^-$), and grow and accumulate excessively. This imbalance in cell growth and death rates eventually leads to fatal immune and neuronal deficiency syndromes with subsequent transformation in some cells.

Methods are provided for the treatment of these intestinal diseases that are related to oxidative stress in subjects suffering from HIV-AIDS. A therapeutically effective amount of a phthalazinedione may be administered to a subject having an intestinal environment with an imbalanced redox state that results from HIV infection. The oxidative stress related to the intestinal disease is modulated by the phthalazinedione. The imbalance redox state is returned to a state of homeostasis upon administration of the phthalazinedione.

Suitable phthalazinediones are provided in U.S. patent application Ser. No. 12/701,088 filed on Feb. 5, 2010 and U.S. patent application Ser. No. 12/025,193 filed on Feb. 4, 2008, and U.S. Pat. No. 7,326,690 filed on Aug. 8, 2005 and U.S. Pat. No. 6,953,799 filed on Oct. 30, 2002; all of which are herein incorporated by reference in their entirety.

In certain specific embodiments of the invention, the phthalazinedione has a purity of at least 95% or more preferably 99%. In certain other specific embodiments, the phthalazinedione has a purity of at least 99.6%. In further embodiments of the present invention, the final phthalazinedione product is a monosodium luminol having a purity of at least 99%. In certain other embodiments of the present invention, a pharmaceutical grade product is provided that is monosodium luminol having a purity of at least 99.6%.

The ts1 retrovirus causes thymic atrophy, CD4+ T cell loss, body wasting, and death, within ~30-40 days postinfection (dpi). In mice infected with ts1, treatment with GVT delayed T cell loss and thymic atrophy for many weeks. Body wasting and death of the infected and treated mice does not occur until well after the infected and untreated control mice have died. GVT treatment of ts1-infected mice maintains the thymic epithelial cell (TEC) cytoarchitecture and cytokeratin gradients required for thymocyte differentiation. It also suppresses thymocyte reactive oxygen species (ROS) levels, upregulates and stabilizes levels of the antioxidant-regulating transcription factor Nrf2, and prevents accumulation of $gPr80^{env}$ (the precursor protein for ts1).

In CNS astrocytes and thymocytes infected with ts1, inefficient cleavage of the viral envelope $gPr80^{env}$ cause it to accumulate in infected cells. In cell types that process $gPr80^{env}$ normally, ts1 infection does not cause cell death. In cells that do die after ts1 infection, the accumulated $gPr80^{env}$ initiates an unfolded protein response (UPR). The UPR in turn cause endoplasmic reticulum stress (ERS). ERS cause the release of Ca2+ from cytoplasmic stores, obligatory loading of this $Ca^{2+}$ into mitochondria which in turn causes mitochondria stress, and finally by profound oxidative stress, leading to apoptosis. The ts1 target cells (i.e., astrocytes, thymocytes, and CD4+ T cells) are not killed by virus infection per Se, but instead die by apoptosis caused by oxidative stress.

The present invention provides methods of treating a subject infected with HIV AIDS with GVT such that epithelial cell organization is maintained. In certain embodiments, GVT is co-administered with HAART treatment. In some embodiments methods are provided wherein epithelial cell organization in ts1-infected mice is treated.

As shown in the exemplifications, apoptosis is elevated in TECs and thymocytes of thymi ts1-infected mice, but not in ts1-infected mice treated with GVT. The present invention provides methods of treating a subject infected with HIV-AIDS that include administering GVT to the subject such that apoptosis in TECs and thymocytes is not elevated. In certain embodiments, GVT is co-administered with HAART treatment.

The exemplification also indicates that thymocyte numbers and weight are dramatically reduced in the ts1-only thymus, but not in thymi of ts1 infected mice treated with GVT. In some embodiments, methods are provided wherein a subject infected with HIV-AIDS is treated by administering an effective amount of GVT to the subject, such that thymocyte numbers and weight are not reduced. In some embodiments, GVT is co administered with HAART treatment.

Also shown is that ROS levels are reduced in thymi for GVT-treated mice. Accordingly, some embodiments of the present invention provide methods for treating a subject infected with HIV-AIDS that include administering GVT to the subject such that ROS levels are reduced in thymi. In some embodiments, GVT is co-administered with HAART treatment.

Nrf2 is shown herein to be upregulated and stabilized in TECs of thymi in GVT treated and ts1-infected mice. In some embodiments, methods are provided wherein a subject infected with HIV-AIDS is administered an effective amount of GVT wherein Nr12 is upregulated and stabilized in TECs of thymi. In some embodiments, GVT is co administered with HAART treatment.

It was also discovered that $gPr8O^{env}$ is processed normally in thymocytes of infected, GVT-treated mice. In some embodiments of the present invention, methods are provided wherein a subject infected with HIV-AIDS is treated with GVT such that $gPr80^{env}$ is processed normally in thymocytes of the subject infected with HIV-AIDS. In some embodiments, GVT is co-administered with HAART treatment.

The known T cell-tropic retroviruses of vertebrates include Type C or D retroviruses and many lentiviruses Some of these agents cause leukemias and lymphomas after an 8-10 months long latent period in their host species, while others cause fulminant diseases that lead to death within weeks of infection. Interestingly, although HIV-I and the lentivirus simian immunodeficiency virus (SIV) use CD4 as their surface receptor on T cells, other T cell-tropic retroviruses do not. Despite this, thymic atrophy, selective infection and killing of CD4+ T-lineage cells, or neoplastic transformation of thymocytes, are common characteristics of diseases caused by these viral agents. At present, the cause of T cell death after infection by these viruses is unknown.

Because of the disease ts1 causes, this agent falls into the group of acute cytopathic retroviruses identified above, although its parent strain MoMuLV-TB has a long latent period, and, like other long-latency leukemia viruses, it causes T cell neoplasia rather than T cell death. When used to infect newborn mice of susceptible strains, the ts1 virus induces a neurodegenerative and immunosuppressive syndrome with many features in common with HIV-AIDS. During its short disease course, ts1 selectively infects and kills peripheral CD4+ T cells although its receptor on T cells is not CD4, but instead is the cationic amino acid receptor MCAT-1. This CD4+ T cell loss leads rapidly to immunodeficiency, wasting and death. If infection is delayed for days or weeks after birth, or if lower virus doses are used to infect newborn pups, the latent period to disease can be prolonged by many months, although the disease, once it develops, has a rapid course similar to that caused by higher doses of ts1.

In CNS astrocytes and thymocytes infected with ts1, inefficient cleavage of the viral envelope preprotein $gPr80^{env}$ causes it to accumulate in infected cells In cell types that process $gPr80^{env}$ normally (yielding the two mature envelope proteins gp70 and PrP15E), ts1 infection does not cause cell death. In cell types that do die after ts1 infection, accumulated $gPr80^{env}$ initiates an unfolded protein response (UPR), which in turn causes endoplasmic reticulum (ER) stress. This stress leaves the body susceptible to further diseases such as other opportunistic infections, wasting syndrome, dementia, nephropathy, neurological conditions, inflammation, oxidative stress or any combination thereof. The result is release of $Ca^{2+}$ from cytoplasmic stores, obligatory loading of this $Ca^{2+}$ into mitochondria, mitochondrial stress, and finally by profound oxidative stress, leading to apoptosis. Together the present invention shows that ts1-infected target cells, which include astrocytes, thymocytes and CD4+ T cells, are not killed by virus infection per se, but instead die by apoptosis caused by oxidative stress.

The present invention therefore methods of reducing or removing the oxidative stress, thereby preventing the downstream conditions or diseases that are associated with the oxidative stress. In particular, the present invention includes methods for treating oxidative stress caused by any disease state, including HIV-AIDS. Therapeutically effective amounts of phthalazinediones are administered to subjects in need thereof such that the oxidative stress is modulated. In some instances the oxidative stress causes homeostatic imbalances in the intestinal environment. The present invention provides methods, uses, products and compounds containing phthalazinediones for the treatment of the oxidative stress such that the imbalance in the intestinal environment is repaired and homeostasis is returned.

Oxidative stress occurs in cells when the production of reactive oxygen species (ROS) exceeds antioxidant defenses. At low concentrations, ROS participate in cell signaling and stimulate cell proliferation but higher concentrations damage biomolecules in the cell, leading to depletion of reduced thiols, including the cell's major antioxidant, glutathione (GSH) Cellular defense responses to oxidative stress occur in a controlled sequence. Level 1 defenses involve upregulation of superoxide dismutases and catalase, which counter the buildup of H2O2 formed after production of superoxide. If the ROS overload overcomes these defenses, the level 2 defenses are deployed to counteract the depletion of cysteine (a GSH precursor) and 6 GSH that follows a larger ROS challenge. At this time, the transcription factor NF-E2 related factor 2, or Nrf2, is activated. Nrf2 is the central regulatory element controlling the transcription of level 2 cytoprotective genes, via the antioxidant response element (ARE) sequences in their promoter regions.

HIV-AIDS patients, naïve T cells are necessary for generation of immune responses against new variants of HIV-1 as they arise during the disease course. Their exhaustion has been proposed as a primary mechanism for immunosuppression in HIV-AIDS.

The antioxidant compound monosodium luminol (trade name GVT®) significantly delays thymic atrophy, wasting, and death in ts1-infected mice, even though the thymi of GVT-treated mice contain replicating ts1. In ts1-infected mice (ts1-only), we report here that the epithelial cell infrastructure of the thymus is destroyed, that its thymocytes are lost to apoptosis, and that this apoptosis is accompanied by accumulation of $gPr80^{env}$. In infected mice treated with GVT (ts1-GVT), the epithelial cell infrastructure is maintained and the thymocytes remain alive, although they are still infected. This protective effect is associated with marked reduction in thymocyte ROS levels, upregulation and stabilization of the antioxidant transcription factor Nrf2 in the thymic epithelial cells (TECs), and lack of accumulated $gPr80^{env}$ in the thymocytes.

GVT® (monosodium luminol) was provided by Bach-Pharma, Inc., North Andover, Mass. Goat anti-MoMuLV gp70 was from Microbiology Associates, Burlingame, Calif. This antibody recognizes epitopes shared by the mature gp70 viral envelope protein and the precursor preprotein $gPr80^{env}$ Monoclonal rabbit anti-cleaved caspase-3 was from Cell Signaling (Boston, Mass.). Mouse monoclonal anti-Nrf2 was from R&D systems (Minneapolis, Minn.). Polyclonal anticytokeratin-5 (CK5) and monoclonal anti-cytokeratin-8 (CK8) antibodies were from Covance Research (Richmond, Calif.) and the National Institutes of Health Developmental Studies Hybridoma Bank (Iowa City, Iowa), respectively. F1TC and Texas Red conjugated anti-mouse, rat, rabbit and goat antibodies were from Jackson ImmunoResearch (West Grove, Pa.).

5 (and 6)-chloromethyl-2',7'-dichlorodihydrofluorescein diacetate (CM-H2DCFDA; Molecular Probes, Eugene, Oreg.; hereafter called DCFDA), is a cell-permeant indicator for intracellular ROS, including hydrogen peroxide and superoxide. The dye itself is non-fluorescent, but when its acetate groups are removed by intracellular esterases, it is oxidized to form a highly fluorescent derivative, carboxydichlorofluorescein. Freshly isolated thymocytes were prepared from uninfected, GVT-only, ts1-only and ts1-GVT-treated mice, at 30 dpi. The thymocytes were incubated with 10 mM of DCFDA, in culture medium (RPMI 1640) at 37° C. for 30 mm. After this loading period, the cells were washed twice with PBS, lysed, and the fluorescence of their contents measured using a Synergy HT multi-detection microplate reader (BioTek Instruments, Inc., Winoski, Vt.). The data are expressed as means±standard deviation (SD) of relative fluorescence units (against a standard curve) for DCFDA-loaded thymocyte lysates for three mice of each treatment group (See FIG. 16).

FVB/N mice were obtained from Taconic Farms (Germantown, N.Y.). Breeding FVB/N pairs were housed in sterilized microisolator cages and supplied with autoclaved feed and water ad libitum. The microisolators were kept in an environmentally controlled isolation room. For ts1 infection, 4-day-old mice were inoculated intraperitoneally with 0.1 ml of vehicle (mock infection) or with 0.1 ml of a ts1 suspension containing $2\times10^7$ infectious units/ml. Mice infected by this protocol, and at this virus dose, became paralyzed and die at 30-40 dpi. For GVT treatment, animals from the control and ts1 infected groups were divided into two groups each on the day of infection. Infected mice were then divided again into two groups, one of whose individuals received 0.9% normal saline, intraperitoneally, for five continuous days-a-week, followed by two resting days, until the end of the experiment, while the other half of the infected animals received freshly prepared GVT, delivered intraperitoneally at 200 mg/kg body weight/day in 0.9% normal saline. The uninfected mice were also divided into two groups, one receiving saline alone, and the other receiving GVT as described above. No toxic effects are observed at any time at this dose of GVT when it is used without infection. All mice were observed daily for clinical signs of disease, and the mice from all groups were sacrificed at 30 dpi.

Whole thymi that were to be used for Western blotting were removed, snap frozen in liquid nitrogen and stored at $-80°$ C. until use. For immunohistochemistry, thymi were snap-frozen in liquid nitrogen in Optimal Cutting Temperature (OCT) embedding compound (Sakura Finetek USA, Torrance, Calif.). These experimental protocols were approved by The University of Texas M.D. Anderson Cancer Center's Institutional Animal Care and Use Committee.

Western blotting analysis was performed as described previously. Briefly, proteins from whole thymic tissue or from isolated thymocytes were extracted with radioimmunoprecipitation assay buffer (1% NP40, 0.5% sodium deoxycholate, 0.1% sodium dodecyl sulfate, 0.25 mM phenylmethylsulfonylfluoride, 1 mg/ml aprotinin, leupeptin, and pepstatin A, 1 mM sodium orthovanadate, and 1 mM sodium fluoride in phosphate-buffered saline, or PBS). Protein concentrations were measured using Bio Rad Dc protein assay reagent (Bio-Rad Laboratories, Hercules, Calif.) as per the manufacturer's instructions. The lysates (30 total protein per sample) were electrophoresed on 10% SDS-PAGE gels, and then transferred to polyvinylidene difluoride membranes (Millipore Corp, Bedford, Mass.). The membranes were blocked at room temperature for 1 h in Tris-buffered saline, or TBS, with 5% non-fat milk, and incubated with a primary unconjugated primary antibody (Santa Cruz Biotechnology, Santa Cruz, Calif.) for 2 h, followed by 3 washes with TBS. The blots were then incubated with horseradish peroxidase-conjugated secondary antibody for an additional 1 h. After three washes, immune complexes were detected by chemiluminescence (NEN Life Science Products, Boston, Mass.). Amonoclonal anti-Il-actin antibody (Sigma, St. Louis, Mo.) was used as a loading control. In Western blots for which fold differences of bands were calculated, the densitometry readings for the bands were first normalized against the $\beta$-actin densities for the same lanes, and then the ratio obtained from this calculation set as 1 for bands for cells or tissues from uninfected mice, and the other values calculated as the ratio of their normalized values against this number.

Dissected tissues were snap-frozen in OCT medium and kept at $-80°$ C. prior to cutting of 5-serial frozen sections. The sections were placed on microscope slides, and the slides kept at $-80°$ C. prior to staining. For staining, the sections were thawed at room temperature for 30 min, fixed in ice-cold acetone for 5 min, washed, and incubated overnight at $4°$ C. with optimum dilutions of primary antibodies. The slides were then washed and incubated in FITC-conjugated or TxR-conjugated anti-rabbit, anti-rat, or antigoat IgG Fab'2. Where double immunostaining was done, it was with polyclonal or monoclonal antibodies raised in cells or animals from two different species, followed by FITC-conjugated anti-IgG for one species, and TxR-conjugated anti-IgG for the other. After incubation in the secondary reagents and washing, the sections were mounted in mounting medium (Vector Laboratories, Burlingame, Calif.) for viewing under an Olympus fluorescence microscope. Control sections were incubated (a) in affinity-purified goat, rabbit or rat IgG, depending upon the host species of the primary antibody, (b) with appropriate isotype controls, for monoclonal antibodies, (c) in secondary antibodies alone, without primary reagents. Optimum staining conditions were developed for each antibody, so that no specific binding was observed in sections incubated in control reagents, while specific binding was observed with the primary antibodies under test.

Western blotting experiments were repeated at least three times, and immunostaining studies were repeated at least twice, to verify reproducibility of results. Quantitative differences between groups in graph-displayed data were compared for statistical significance Student's t-test. p-values of less than 0.05 were considered statistically significant.

Epithelial cell organization is disrupted in the thymi of ts1-infected mice, but maintained in infected mice treated with GVT.

In the normal mouse thymus, the epithelial matrix of the organ is divided into grape-like lobules, each of which is composed of a well-demarcated outer cortical epithelium and an inner medullary epithelial cell area. Both areas are like epithelial cell "baskets" filled with thymocytes and other cell types, including macrophages, dendritic cells, fibroblasts, and a rich connective tissue matrix. In each lobule, T cell precursors arrive in the thymus from the bone marrow, landing in the corticomedullary junction (CMJ) between the cortex and medulla. The subsequent differentiation of the T cell precursors into mature T cells then occurs in the context of this corticomedullary structure, during which time the thymocytes travel from the CMJ through the cortex to the outer edge of the lobule, and then come back again, all the while undergoing a scheduled differentiation sequence that takes them through defined developmental checkpoints. These events are governed by contact-mediated and humoral reciprocal crosstalk between the TECs and thymocytes The epithelial thymus contains two distinct kinds of cells: a simple epithelium in the cortex, and a basal epithelium in the medulla. Normal corticomedullary organization of the murine thymus has a molecular component that can be assessed using antibodies to cytokeratin markers. Cytokeratins are a diverse family of intermediate filament proteins that distinguish different epithelial cell types, including the two epithelial cell types in the mouse thymus. In the healthy mouse, the cortical epithelial cells express cytokeratin (CK8), the medullary epithelial cells express cytokeratin-5 (CK5), and a small population separating in the CMJ expresses both. The presence of an intact epithelial cell cytokeratin CK8/5 expression gradient, and of a clear corticomedullary boundary in H&E-stained slides, is a precise anatomical correlation of normal thymocyte differentiation.

In the mouse thymus, TEC differentiation is dysregulated if the thymocytes cannot differentiate; likewise, normal thymocytes cannot differentiate in thymi whose epithelium is abnormal (reviewed in. To determine how ts1 infection affects the epithelial and thymocyte compartments in the thymus, and to follow GVT effects on these events, cytoarchitecture and cytokeratin expression patterns for TECs and thymocytes in uninfected, ts1-infected (ts1-only) and infected GVT-treated (ts1-GVT) mice sacrificed at 30 dpi were first compared. Frozen sections from thymi of uninfected and ts1 infected (ts1-only) and ts1-infected, GVT-treated (ts1-GVT) mice were prepared at 30 dpi, and then (1) stained with H&E, (2) doubly immunostained either with anti-CK8 and anti-CK5 (on an uninfected thymus section), or (3) doubly stained with anti-gp70 and CK8 (infected ts1-only or ts1-GVT thymic sections). The left side panel in FIG. 14(A) is an H&E-stained section of thymus from an uninfected mouse. It shows clear lobular cortimedullary epithelial organization, and the left immunostained section in FIG. 14(B), which also is from an uninfected mouse thymus, shows correct epithelial cytokeratin organization (CK8-positive cortex, CK5-positive medulla). In the ts1-only sections in the middle panel of FIG. 14(A), severe cortical thinning is evident in the H&E-stained section, and the corresponding immunostained section in FIG. 14(B) (see box in H&E section) shows that CK5-positive medullary epithelial cells are not confined to the medulla as they are in the normal thymus, but instead are growing out into the thinning thymic cortex. FIGS. 14(A) and (B) also shows sections from the thymic cortex of a 30 dpi ts1-GVT mouse (right). The H&E stained section has normal corticomedullary organization. The immunostained ts1-GVT section (also see box in FIG. 14(A)) contains large, apparently uninfected (red, not yellow) CK8+ TECs within in an intact CMJ boundary (extending from lower left to upper right in the panel). In the same section, gp70-positive thymocytes surround the TECs.

Apoptosis is elevated in TECs and thymocytes of thymi ts1-infected mice, but not in infected mice treated with GVT.

Caspase-3 is the executive enzyme that completes apoptotic cascades in most cell types. The presence of the activated (cleaved) form of caspase-3 is a specific indicator of apoptotic cell death in tissues, including the thymus. In the ts1-only and ts1-GVT sections stained for CK8 and gp70 in FIGS. 14(A) and (B), the TECs and thymocytes appear dead in ts1-only section, but are apparently alive in ts1-GVT sections. To confirm this, levels of activated caspase-3 protein in thymocytes from these animals were compared. The Western blot in FIG. 15(A) shows that ts1-only thymocytes contain elevated amounts of cleaved caspase-3, relative to uninfected thymocytes, while ts1-GVT thymocytes have somewhat less cleaved caspase-3, in relation to the ts1-only tissues. It should be noted that the relatively high levels of cleaved caspase-3 in uninfected thymocytes are normal, because most T cells generated in the thymus also undergo apoptosis there Thus, if the ts1-GVT thymus is functioning normally, cleaved caspase-3 levels should approach those of uninfected thymi, as they apparently do (FIG. 15(A)).

For an in situ look at caspase-3 in the thymi the three groups above, we stained thymic sections for gp70 or for cleaved caspase 3. The photomicrographs in FIG. 2(B) show that cells positive for gp70 are abundant in thymi from both ts1-only and ts1-GVT mice. However, while cleaved caspase-3-positive cells are abundant in the ts1-only thymus section, they are apparently absent in the ts1-GVT section.

Thymocyte numbers and weight are dramatically reduced in the ts1-only thymus, but not in thymi of infected mice treated with GVT.

The loss or presence of cytokeratin-based corticomedullary organization in ts1 only thymi (FIG. 14), and the presence or absence of cleaved caspase-3 in these tissues (FIG. 15) are reliable but indirect markers of dysregulated (ts1-only) vs. apparently normal (ts1-GVT) T cell differentiation. To assess the state of T cell differentiation directly, we compared the total numbers of thymocytes, and thymic weights, for 30 dpi mice from the uninfected, GVT-only, ts1-only, and ts1-GVT treatment groups. Similarly, when average thymus weights for the same mice, prior to isolation of their thymocytes were compared, it was observed that a significant loss of thymus weight in the thymi of ts1-only mice. However, no thymic weight loss had occurred in 30 dpi infected mice if they had also been treated with GVT. A small but significant weight increase was evident in the ts1-only thymi, relative to the uninfected controls ($p<0.05$).

Figure 16:
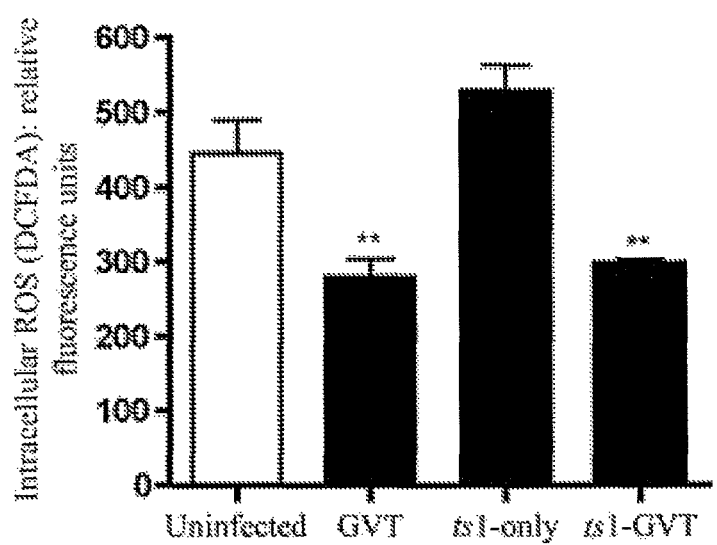
FIG. 16 is a diagram of thymocyte ROS content.

ROS levels are reduced in thymi of GVT-treated mice. Oxidative stress is the trigger for apoptosis of ts1-infected astrocytes and oxidative stress also occurs in thymi of ts1-infected mice, but GVT treatment prevents both astrocyte and thymocyte death in situ. Using the fluorescent dye DCFDA to quantitate the thymocyte content of ROS, the effects of GVT treatment of mice on the intracellular redox conditions in their thymocytes was examined. The bar graphs in FIG. 16 show that thymocytes from GVT-treated mice do have significantly lower ROS contents than thymocytes from uninfected mice, whether the mice are infected or uninfected or not ($p<0.001$, when compared either to uninfected or ts1-only thymocytes). These observations tell us two new and significant things: one, the ROS-lowering effects of GVT do not require concomitant infection with ts1 or other oxidant stressors, and, two, that GVT treatment somehow sets up a conditions in which a steady state redox "tone" is established and maintained in thymocytes of infected treated animals, thus presumably affecting all intracellular parameters impacted by ROS levels in the cells. These results link GVT protection of the thymus to events that reduce ROS levels in thymocytes, and they suggest that GVT protects thymocytes by setting up low-ROS conditions that allow ts1 infection of thymocytes, but prevent the cytopathology and apoptosis that otherwise would kill the infected cells.

Nrf2 upregulation and stabilization in TECs of thymi from GVT-treated, infected mice. When cultured astrocytic cells are infected in culture with ts1, about 50% of the cells die, but 50% remain alive, and these can be passaged over a long period of time. Notably, the astrocytes that survived were different from those that died, with respect to (a) their maintenance of low steady-state ROS levels, and (b) their high levels of Nrf2. These results suggested that the high Nrf2 levels in ts1-infected astrocytes were causally linked to their low ROS.

Many cell types, including astrocytes, maintain ambient levels of the Nrf2 protein, which is a transcription factor that coordinately upregulates many genes that participate in Phase 2 antioxidant defenses. In non-stressed cells, Nrf2 is held in an inactive state as part of a complex with the Keap-1 molecule. As long as steady-state conditions prevail, the complexed Nrf2 is cyclically ubiquitinated, released to the proteasomes for degradation, and replaced by newly translated Nrf2. When oxidant stress conditions occur, however, redox-sensitive sites on the Keap-1 protein allow it to release Nrf2, which is then phosphorylated and transported to the nucleus. In the nucleus, Nrf2 activates genes that have antioxidant response element (ARE) sequences in their promoters.

When ROS levels in the cells are returned to normal, it has been assumed that the activated Nrf2 that is left is ubiquitinated and degraded. However, Nrf2 levels can be stabilized in the cytoplasm and nucleus under certain kinds of oxidant stress conditions or by drugs that inhibit Nrf2 degradation in proteasomes. Agents that stabilize Nrf2 levels in cells have been identified as having anti-inflammatory effects, most likely due to the continued or amplified antioxidant defenses that might be available to cells as a consequence.

There are many non-thymocyte cell types in the normal thymus, including dendritic cells, macrophages, and TECs.

Dendritic cells, for example, control T cell activation events via the T cell receptor, by regulating the redox environment of antigen presentation and recognition In thymi of ts1-GVT mice, the cells most likely to play a supporting role on this type would be the TECs. In addition to hosting thymocyte differentiation, TECs provide metabolic and redox support to thymocytes via Nrf2 stabilization and release of thiol redox antioxidants to thymocytes, just as astrocytes do for neurons in the CNS under oxidant stress [

Thymocytes of FVB/N mice can be cultured and infected by ts1 in vitro, but only if IL-2 and IL-7 (produced by thymocytes and TECs, respectively) are added to the culturing medium, and only if the culturing wells contain thymic remnants. HIV-1 produce similar results, in showing that TECs must be present for infection of cultured thymocytes. For ts1 and HIV infection of cultured thymocytes, therefore, TECs are required to make virus available for thymocyte infection, or to provide metabolic or redox support for infected thymocytes. For the same reasons, GVT protection of thymocytes require the presence of TECs that can upregulate and stabilize their Nrf2. For example, when sections of uninfected ts1-only vs. ts1-GVT thymi are frozen and doubly stained with gp70 and Nrf2 the results of FIG. 18(C) are obtained. The photomicrographs in FIG. 5(C) show that the ts1-only thymic section contains many large, infected gp70-positive cells, all of which also contain Nrf2 (no red cells are present, indicating that all Nrf2-positive cells are also infected). By contrast, the thymic section from the ts1-GVT mouse shows many gp70-positive infected cells, but also has large numbers of red cellular profiles (Nrf2-positive only) that are not thymocytes.

gPr80$^{env}$ is processed normally in thymocytes of infected, GVT-treated mice. One consequence of low-ROS conditions in thymocytes of ts1-GVT mice might be the normal processing of gPr80$^{env}$ to gp70 and PrP15E in infected thymocytes. As noted above, ts1-infected astrocytes and thymocytes die as a consequence of accumulation of the mutant ts1 preprotein gPr80$^{env}$ in the ER. Accumulation of gPr80$^{env}$ triggers the UPR, which in turn elicits ER stress and calcium loading into mitochondria, causing mitochondrial and oxidant stress-induced apoptosis. In normal cells, the local redox environment in the ER is controlled to provide reducing conditions necessary for formation of disulfide bonds, and to promote or inhibit hydrogen bonding during the translation of proteins with complex folding requirements. The present invention further examines whether the low-ROS conditions in ts1-only thymocytes might allow normal folding and processing of the ts1 mutant gPr80$^{env}$. This would protect them from the apoptotic cascades that are activated in thymocytes of ts1-only mice.

To determine whether this occurs, for example, Western blotting with anti-gp70 is used to compare amounts of gPr80$^{env}$ (uncleaved) to gp70 (cleaved) envelope protein in thymocytes of ts1-only vs. ts1-GVT mice. The results in FIG. 17 show that ts1-only infected tissues contain both aggregated gPr80env at 80 kDa, and processed gp70, at 70 kDa. By contrast, all of the gp70-immunoreactive protein is in the 70 kDa band from thymocytes of ts1-GVT mice, indicating that the gPr80$^{env}$ is being processed normally in these cells.

Like ts1, other cytopathic retroviruses, including HIV-1, SIV and FIV, cause damage to thymic cytoarchitecture and loss of thymocytes in their respective host species, making the thymus unable to supply naïve T cells for protective immune responses to viral variants as they appear during the disease course. HAART therapies, like those currently in use for treatment of HIV-AIDS, may not restore thymopoiesis even assuming that normal T progenitor cells are produced and sent to the thymus from the bone marrow in these patients. This means that naïve T cell exhaustion, thought to be one cause of HIV-1 immunosuppression might still occur under HAART treatment. The present invention therefore provides that TEC and thymocyte loss following ts1 retroviral infection are not the results of infection per se, but rather are the result of oxidative stress leading to apoptosis of thymocytes. If oxidative stress also occurs in the HIV-AIDS thymus and thymocytes, and if GVT can reduce or eliminate it even as the cells remain infected, then repopulation of the thymus might be possible in these patients, either by autologous bone marrow T cell progenitors or by transplanted bone marrow stem cells.

GVT is an antioxidant compound that has anti-inflammatory and anti-apoptotic properties in many animal and human diseases. GVT is also a non-toxic drug in mice and humans. In ts1 infection, the thymus appears to be a “staging area” from which infectious virus is disseminated to other tissues, including the CNS; in fact, a thymus must be present if CNS and then systemic infection are to occur. For example redox imbalance in portions of the thymus have been demonstrated to cause similar imbalance or inflammation in other remote organs such as the eye.

The survival and apparent homeostasis of its TEC and thymocyte cell compartments, under GVT treatment, could be the basis of what becomes either a fetal disease or a harmless infection in other tissues as well. In the ts1-GVT thymus, it is demonstrated herein (1) that the thymic epithelial maintain normal characteristics in ts1-GVT mice; (2) that thymocytes of ts1-GVT mice survive despite continued infection; (3) that the thymocytes have lower than normal ROS levels; (4) that TEC Nrf2 levels are upregulated and stabilized; and (5) that these thymocytes do not contain accumulated gPr80$^{env}$ If the first of these is causally linked in series to the last, then the pro-survival effects of low ROS conditions, caused by GVT, could either be direct (via GVT alone) or indirect, via GVT upregulation and stabilization of Nrf2.

Given that other retrovirus infections involve oxidative stress, GVT treatment prevents thymocyte loss and maintain normal thymic cytoarchitecture in all cytopathic retroviral diseases. The ts1-infected mouse is a model for HIV-AIDS, although there are some differences between the two viruses and the diseases they cause. Matching characteristics between the ts1-infected mouse and the HIV-infected human have been identified in published papers from our laboratory and from others. The ts1 virus selectively infects and kills CD4+ peripheral T cells and CD4+ thymocytes.

Some studies over the past decades suggest that abnormal viral protein accumulation and/or oxidative stress in loss of T cells in HIV-AIDS. Recent work has shown that folding of nascent membrane proteins in the ER of healthy cells depends upon a carefully controlled intracellular redox environment. In cells whose ROS levels have risen due to oxidant challenge, misfolding theoretically is a possibility for all membrane proteins in the cell. In light of this, it is interesting to note that the HIV-1 membrane preprotein gp160 has particularly strict requirements for sequential and complex folding events and that these make it especially likely to misfold and aggregate when ROS levels increase in infected cells. Since ts1 gPr80env misfolds in thymocytes whose ROS levels are near normal or only slightly elevated (FIGS. 16 and 17), the lowering of ROS caused by GVT treatment in thymocytes of ts1-GVT mice may promote normal folding of gPr80$^{env}$. If this occurs, it may be why TECs and thymocytes in ts1-GVT mice survive infection (FIG. 8). The findings reported suggest that abnormal protein accumulation, followed by oxidative stress, might lead to the killing of thymocytes and T cells in HIV-AIDS and in other retroviral syndromes that target these cells. GVT and other antioxidant compounds will allow maintenance or restoration of a normal thymic microenvironment in HIV-AIDS patients, allowing the differentiation of autologous bone marrow T cell progenitors, or of T cell progenitors from bone marrow or stem cell allotransplants. As an antioxidant, GVT is presented herein as a therapeutic utility as a non-toxic anti-inflammatory drug that exploits natural antioxidant mechanisms (e.g., Nrf2) to prevent tissue damage after oxidant injury.

EXEMPLIFICATION

The invention will be further understood by the following examples. However, those skilled in the art will readily appreciate that the specific experimental details are only illustrative and are not meant to limit the invention as described herein, which is defined by the claims which follow thereafter. The contents of any patents, patent applications, patent application publications and references cited throughout this specification are hereby incorporated by reference in their entireties.

Example 1

Monosodium Luminol (GVT) Preserves Crypt-Villus Epithelial Organization in ts1-Infected Mice In certain exemplary demonstrations of the invention, the following virus, antibodies, agents, mice infection and drug treatments were employed with to obtain the results demonstrated in the figures and discussed herein.

The ts1 virus, a mutant of MoMuLV, was propagated in TB cells, a thymus-bone marrow cell line, and titered on 15F cells, as previously described.

GVT® (sodium a-luminol) was provided by Bach-Pharma, Inc., North Andover, Mass. Goat anti-MoMuLV gp70 was from Microbiology Associates, Burlingame, Calif. (this antibody recognizes epitopes shared by the mature gp70 viral envelope protein and the precursor preprotein $gPr80^{env}$). Anti-mouse Ki67 was from Vector Laboratories, Burlingame, Calif. Polyclonal and monoclonal anti-mouse TSHl3 were from Cell Signaling (Boston, Mass.) and Dr. John R. Klein's laboratory, respectively. Mand rabbit anti-activated caspase-3 was from Cell Signaling. Mouse monoclonal anti Nrf2 was from R&D systems (Minneapolis, Minn.). FITC and Texas Red-conjugated anti-mouse, rat, rabbit and goat antibodies were from Jackson ImmunoResearch (West Grove, Pa.).

FVB/N mice were obtained from Taconic Farms (Germantown, N.Y.). Breeding FVB/N pairs were housed in sterilized microisolator cages and supplied with autoclaved feed and water ad libitum. The microisolators were kept in an environmentally controlled isolation room. For ts1 infection, four-day-old mice were inoculated intraperitoneally with 0.1 ml of vehicle (mock infection) or with 0.1 ml of a ts1 suspension containing 2×107 infectious units/ml. Mice infected by this protocol, and at this virus dose, become paralyzed and die at 30-40 dpi [2]

For GVT treatment, animals from the control and ts1-infected groups are divided into two groups each at 2 dpi. The infected mice are then divided again into two groups, one of whose individuals received 0.9% normal saline, intraperitoneally, five continuous days a week, followed by two resting days, until the end of the experiment. At the same time, mice from the other half of the infected animals received freshly prepared GVT, delivered intraperitoneally at 200 mg/kg body weight/day in 0.9% normal saline. The uninfected mice were also divided into two groups, one receiving saline alone, and the other receiving GVT as described above. No toxic effects were observed at any time at this dose of GVT when it was used without infection.

At 30 dpi, mice from all groups were sacrificed, and their small intestines (2 cm from the jejunum) processed for Western blotting of the tissues or for frozen section immunohistochemistry. All mice were observed daily for clinical signs of disease, and individuals from all groups were sacrificed at 30 dpi. Intestinal tissues to be used for Western blotting are removed, snap-frozen in liquid nitrogen and stored at −80° C. until use. For immunohistochemistry, intestine segments were snap-frozen in liquid nitrogen in OCT embedding compound. These animal protocols were approved by The University of Texas M.D. Anderson Cancer Center Institutional Animal Care and Use Committee.

Western blotting analysis was performed as described previously. Briefly, whole cell protein was extracted from whole intestines in radioimmunoprecipitation assay buffer (NP40, 0.5% sodium deoxycholate, 0.1% sodium dodecyl sulfate, 0.25 mM phenylmethylsulfonylfluoride, 1 mg/ml aprotinin, leupeptin, and pepstatin A, 1 mM sodium orthovanadate, and 1 mM sodium fluoride in phosphate-buffered saline, or PBS). Protein concentrations were measured using the Bio-Rad Dc protein assay reagent (Bio Rad Laboratories, Hercules, Calif.) as per the manufacturer's instructions. These lysates (30 mg total protein per sample) were electrophoresed on 10% SDS-PAGE gels, and then transferred to polyvinylidene difluoride membranes (Millipore Corp, Bedford, Mass.). The membranes were blocked at room temperature for 1 hr in tris-buffered saline, or TBS, with 5% nonfat milk, and incubated with unconjugated primary antibody for 2 hrs, followed by 3 washes with TBS. The blots were then incubated with species-appropriate horseradish peroxidase-conjugated secondary antibody for an additional 1 hr. After three washes, immune complexes were detected by chemiluminescence (NEN Life Science Products, Boston, Mass.). A monoclonal anti-13-actin antibody (Sigma, St. Louis, Mo.) was used as a loading control. Values calculated as the ratio of their normalized values against this number. Western blotting experiments were repeated at least three times, to verify reproducibility of results.

Dissected tissues were snap-frozen in OCT medium and kept at −80° C. prior to cutting of 5 urn-thick serial frozen sections. The sections were placed on microscope slides, and the slides kept at −80° C. prior to staining. For staining, the sections were thawed at room temperature for 30 mm, fixed in ice-cold acetone for 5 mm, washed, and incubated overnight at 4° C. with optimum dilutions of primary antibodies. The slides were then washed and incubated in FITC-conjugated or TxR-conjugated Fab'2 fragments of anti-rabbit, anti-rat, or anti-goat IgG. Where double immunostaining was done, it was with polyclonal or monoclonal antibodies raised in cells or animals from two different species, followed by FITC-conjugated anti-IgG for one species, and TxR-conjugated anti IgG for the other. After incubation in the secondary reagents and washing, the sections were mounted in mounting medium (Vector Laboratories, Burlingame, Calif.) for viewing under an Olympus fluorescence microscope. Control sections were incubated (a) in affinity-purified goat, rabbit or rat IgG, depending upon the host species of the primary antibody, (b) with appropriate isotype controls, for monoclonal antibodies, (c) in secondary antibodies alone, without primary reagents. Optimum staining conditions were developed for each antibody, so that no specific binding was observed in sections incubated in control reagents, while specific binding was observed with the primary antibodies under test. Immunostaining studies were repeated at least twice, to verify reproducibility of results.

Crypt-vu/us organization and T cell numbers are abnormal in intestines from ts1-only mice, but not from those ts1-GVT animals.

Figure 2:
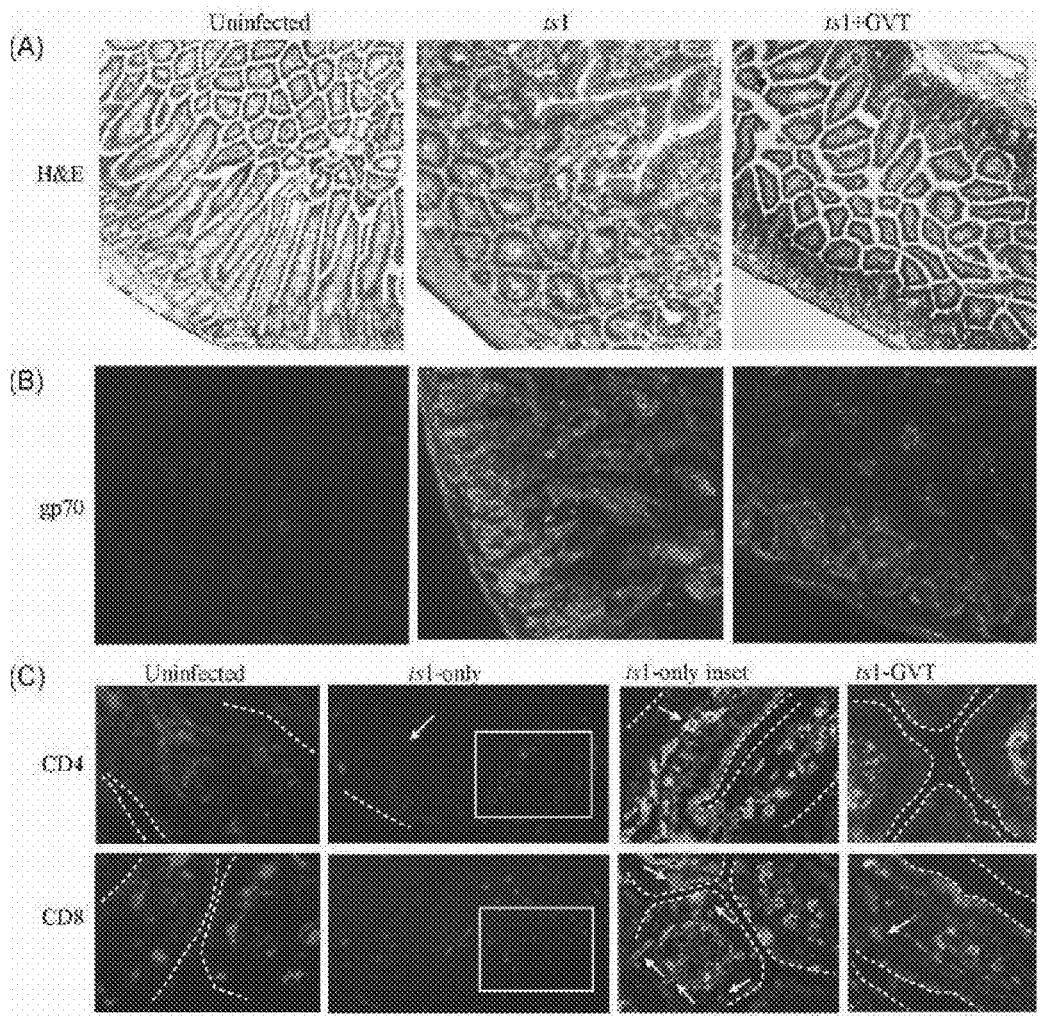
FIG. 2 is a diagram of loss of crypt-villus organization, ts1 infection and depletion of CD4+ cells in the intestines of ts1-only mice, and maintenance of normal parameters and cell numbers, in 30 dpi uninfected, ts1-only and ts1-GVT mice.

FIG. 2 shows frozen sections of small intestines from 30 dpi uninfected, ts1 only and ts1-GVT mice, stained with hematoxylin and eosin (H&E) for cytoarchitecture (A), with anti-gp70 to identify infected cells (B), and with anti-CD4 or anti-CD8 to identify cells in the LP of the villi (C). The H&E panels show extensive hyperproliferation of the crypts in the ts1-only intestine. Together with CD4+ T cell loss, crypt epithelial hyperproliferation, followed by intestinal collapse, is a common intestinal manifestation of infection by other retroviruses, including SHIV and SIV in nonhuman primates, FIV in cats, and HIV-1 infection in humans. Remarkably, however, the H&E and gp70-stained ts1-GVT intestine images in FIG. 2 show apparently normal crypt-villus organization at 30 dpi, despite the presence of many infected cells in the LP. CD4-positive cells are abundant in the LP regions of uninfected intestinal villi, virtually absent in the ts1-only villi, but present in the LP of villi in the section from a ts1-GVT mouse. CD8-positive cells are reduced in number in the ts1-only mouse intestines, but they are not depleted from the villi as are CD4-positive cells in the ts1-only mice (C).

The TSH gradient of the crypt-villus axis is lost in the ts1-only intestine, but not in intestines from ts1-GVT mice.

In the hypothalamo-pituitary-thyroid (HPT) axis, the neurohormone thyrotropin releasing hormone (TRH) is produced by the hypothalamus, and delivered to the anterior pituitary gland below. TRH triggers production of thyrotropin by pituitary thyrotroph cells (thyrotropin is the thyroid-stimulating hormone, or TSH). TSH travels through the blood to the thyroid, where it binds to its receptor (the TRHr) on the follicle cells, and these follicle cells and the follicular fluid respond by producing thyroglobulin and iodinated thyroxine (T3 and T4), and by releasing thyroxine into the blood.

Recent work has disclosed that the small intestinal epithelial cells of mice, like pituitary thyrotrophs, express genes for the two subunits of TSH. In addition, a subpopulation of small intestinal T cells (but not peripheral T cells) has surface TSHr. These findings point to a local epithelial-lymphocyte hormone loop, involving TSH produced by crypt epithelial cells, response to this TSH by intestinal T cells, and feedback to the epithelium.

The intestinal epithelial TSH gradient is disturbed during rotavirus and reovirus infection. In both conditions, blocks of enterocytes on the villi re-initiate TSH expression, and groups of LP lymphoid cells aggregate below these cells.

Figure 3:
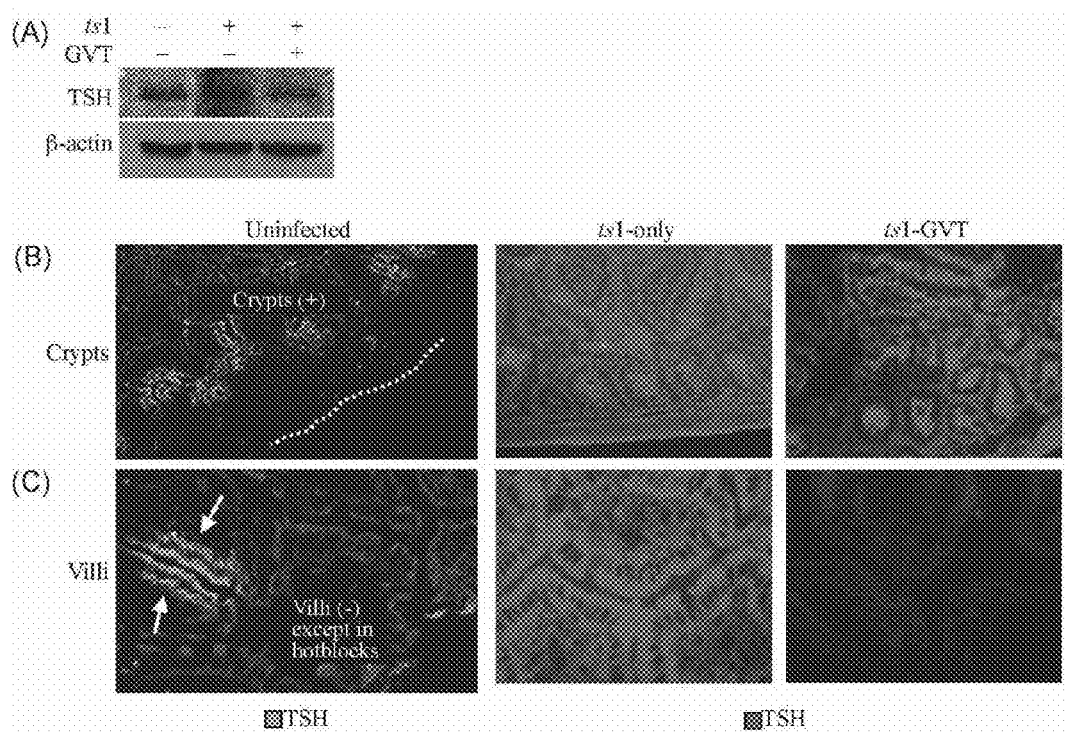
FIG. 3 is a diagram of loss of the epithelial crypt-villus gradient organization for TSH in 30 dpi ts1-only mice, and maintenance of this gradient in age-matched ts1-GVT mice.

To determine whether intestinal epithelial TSH gradients are dysregulated in ts1 infection, TSH levels in intestines from uninfected, ts1-only and ts1-GVT mice were compared. FIG. 3(A) shows a Western blot of lysates from intestines mice of the above three groups, stained for TSH. Uninfected intestinal tissues show an ambient level of TSH expression at 30 days of age, but the ts1-only intestines contain much more TSH, while the ts1-GVT intestines contain what appear to be normal TSH levels. To look at what is happening to TSH gradients at the cellular and tissue level, sections of these intestines were prepared and stained with anti-TSH and anti-gp70. FIGS. 3(B and C) shows that TSH expression is limited to the crypt epithelium in uninfected mouse intestines; that the entire intestinal epithelium, crypts and villi alike, express TSH in the ts1-only intestine: but TSH expression is limited to the crypts in the ts1-GVT intestines.

The distinct cell cycling patterns of the crypt and villus are lost in the ts1-only intestine, but not in intestines from ts1-GVT mice.

A second epithelial cell gradient exists in the healthy small intestine, and this gradient is disrupted in disease conditions affecting this tissue. The cell cycling marker Ki67 is an intermediate filament protein found only in dividing cells. Below the crypt-villus boundary of normal intestines, all epithelial cells covering the villi are dividing. Above this boundary, they are quiescent. When immunostained with antibody against Ki67, epithelial cells in the crypts are Ki67-positive, while those covering the villi are Ki67-negative. Like the epithelial cytokeratin gradients of the thymus (companion paper) and the TSH gradient of the intestine, intact Ki67 expression patterns, distinguishing the crypts and villi, reflect normal T cell differentiation conditions in the LP below the epithelium.

Figure 4:
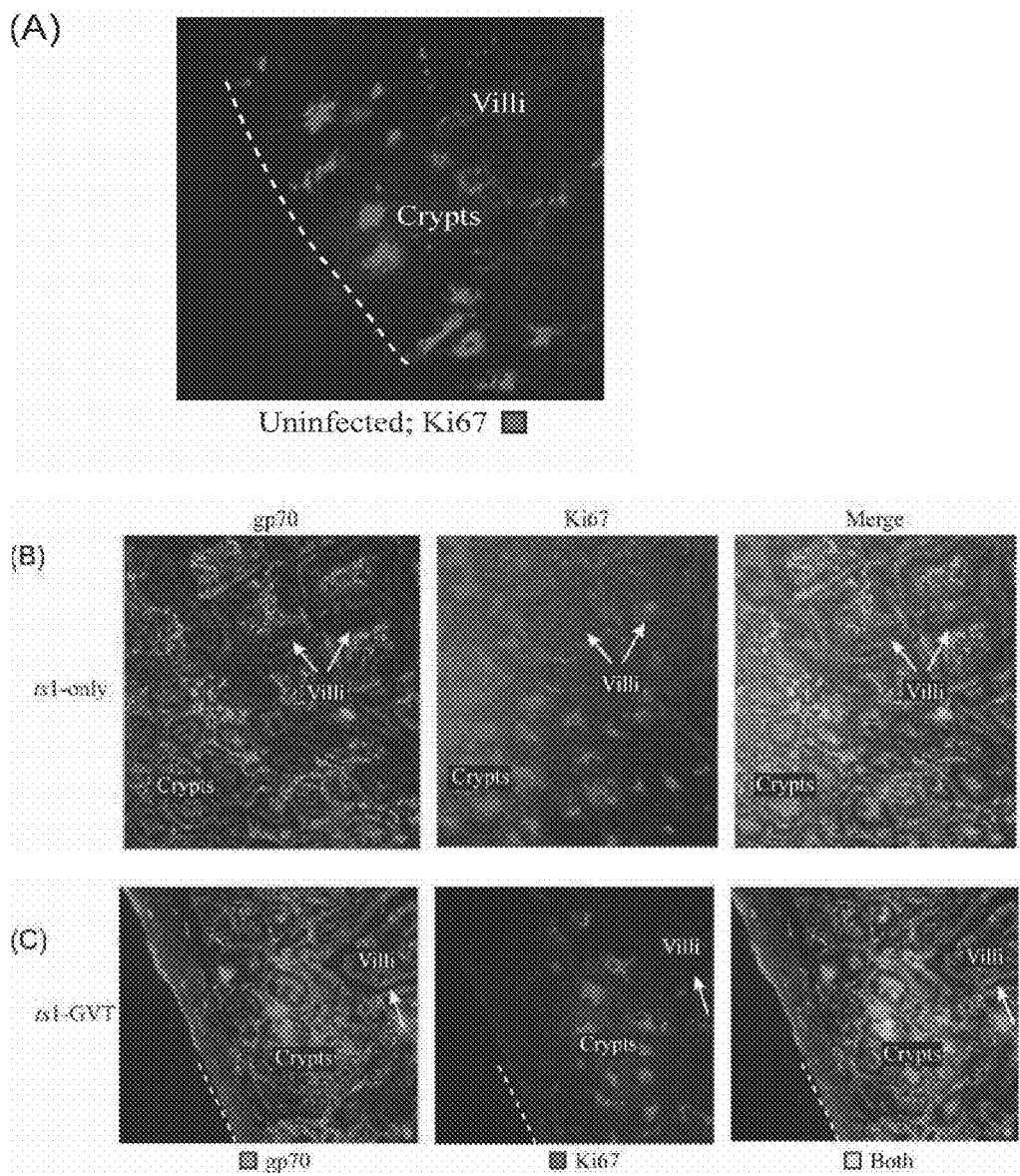
FIG. 4 is a diagram of dysregulation of epithelial crypt-villus Ki67 expression (cell cycling) in 30 dpi ts1-only intestines, and maintenance of these gradients in age-matched ts1-GVT intestines.

To determine whether ts1 infection affects the crypt-to-villus Ki67 gradient, and to find out whether GVT treatment prevents this, one frozen section of an uninfected small intestine is immunostained with anti-Ki67 alone, and then doubly immunostained uninfected, ts1-only and ts1-GVT intestine sections with gp70 and Ki67. The doubly stained sections were photographed under bandpass filters for FITC and then for Texas Red, and a merged image was made from the two single-filter images for the ts1-only and ts1-GVT sections. FIG. 4(A) shows that Ki67 staining is confined to basolateral surfaces of the crypt epithelial cells of normal intestines, as has been reported by others. In both the ts1-only (B) and ts1-GVT sections (C), however, gp70 infected lymphoid cells present in the LP. Ki67 staining is present in epithelial cells of both the crypts and villi of the ts1-only intestines (B). However, while the ts1-GVT section shows Ki67 staining that is limited to the crypts (C), reflecting the presence of a normal Ki67 gradient in intestines from ts1-GVT mice.

In ts1-GVT mice, intestinal epithelial cells contain high levels of the antioxidant transcription factor Nrf2, and their T cells are protected from apoptosis Like many other cell types, intestinal epithelial cells maintain ambient intracellular levels of NFE-2-related factor 2 (Nrf2), which is a transcriptional factor that coordinately upregulates many genes that participate in antioxidant defenses. Under steady-state conditions, Nrf2 is held in an inactive state as part of a complex with another protein called Keap-1. When oxidant stress conditions occur, Keap-1 releases Nrf2, which then is phosphorylated and transported to the nucleus. When it arrives there, Nrf2 for activates genes that have antioxidant response element (ARE) sequences in their promoters.

For some time, it has been assumed that correction of an abnormal-redox situation, once completed, re-establishes the Keap1-Nrf2 complex, bringing Nrf2 levels down again. However, it has been shown that high levels of free Nrf2 can be stabilized in the cytoplasm and nucleus under certain kinds of oxidant stress conditions, or by drugs that inhibit Nrf2 degradation in proteasomes. Chemical agents that stabilize Nrf2 in cells include drugs known to have anti-inflammatory effects, presumably because they may maintain low ROS levels in tissues during long periods of oxidative stress. One objective of the study herein was to determine whether Nrf2 upregulation and stabilization occur in intestines of ts1-only vs. GVT mice.

Figure 5:
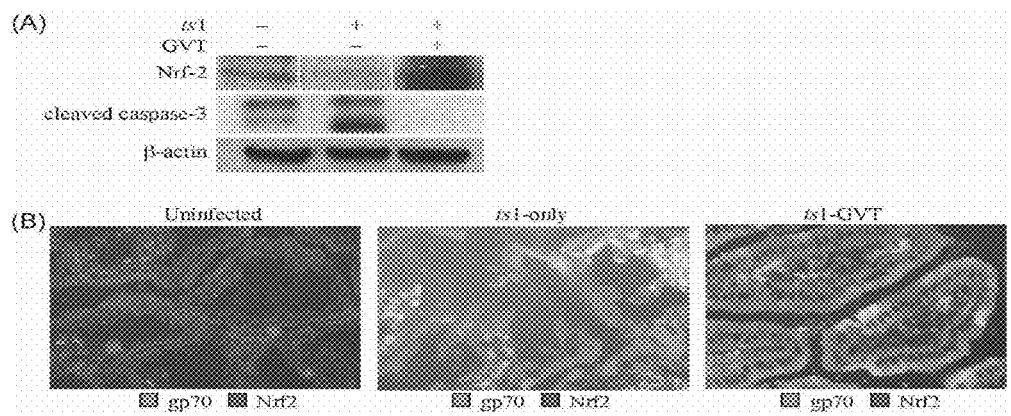
FIG. 5 is a diagram of Nrf2 expression and caspase-3-mediated apoptosis in intestinal lysates and sections from uninfected, ts1-only and ts1-GVT mice.

The Western blot in FIG. 5(A) shows that Nrf2 levels in intestinal tissues of ts1 only mice are slightly lower than those of uninfected intestines, but that they are significantly upregulated in ts1-GVT intestines. To determine which cells are responsible for the increased Nrf2 levels in ts1-GVT intestines, uninfected, ts1-only and ts1-GVT thymi were stained at 30 dpi for gp70 and for Nrf2. FIG. 5(B) shows that the ts1-only section has neither gp70 nor Nrf2 inside any recognizable cells, because the tissues apparently have collapsed, and few intact epithelial cells remain. By contrast, the ts1 GVT intestine contains profiles of apparently healthy villi whose epithelial cells and lymphoid compartments are intact, but whose epithelial cells show heavy loading with Nrf2, and whole LP cells are infected.

It was next determine whether high-Nrf2 conditions in the ts1-GVT intestines might be related to reduced or absent apoptosis in the intestinal tissues of ts1 GVT mice, as they are in the ts1-GVT thymus. Levels of the apoptotic protein cleaved caspase-3 in intestines from uninfected, ts1-only, and ts1-GVT mice were compared. Caspase-3 is the executive enzyme that completes the many different apoptotic cascades that occur in most cell types. The presence of cleaved caspase-3 is a specific indicator of apoptotic cell death in tissues. FIG. 5(A) shows that a low ambient level of cleaved caspase-3 is present in uninfected intestinal tissues, but that high levels of this enzyme are present in intestines of ts1-only mice, where many cells are undergoing apoptosis. By contrast, caspase-3 is absent in the intestines of ts1-GVT mice.

In ts1-GVT mice, accumulated $gPr80^{env}$ is reduced by GVT.

Figure 6:
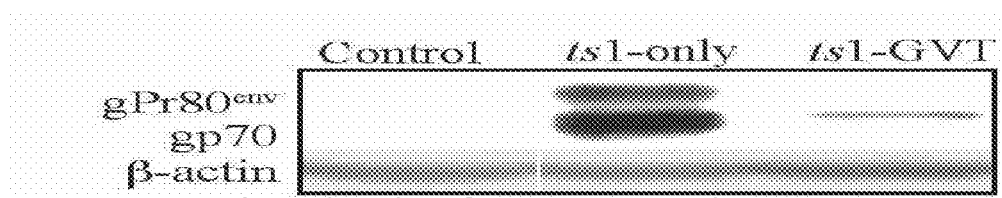
FIG. 6 is a diagram of Western blot of 30 dpi intestinal tissues from uninfected, ts1-only and ts1-GVT mice, probed for gp70.
Figure 7:
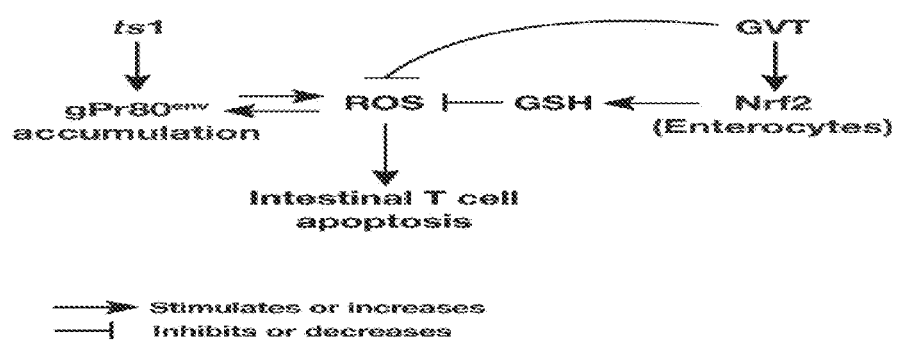
FIG. 7 is a diagram showing possible mechanisms for protection of 30 dpi ts1 infected mouse intestines by GVT.
Figure 8:
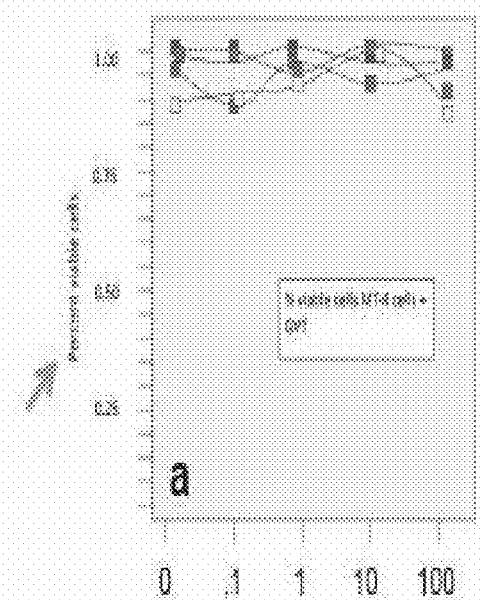
FIG. 8 is a diagram demonstrating the effect of GVT treatment on MT-4 cells in HIV subjects.
Figure 8:
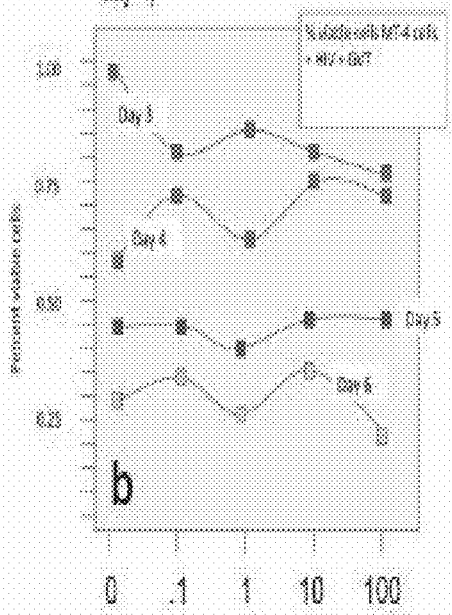

In studies with the thymus, discussed in related application 61/153,908 filed on Feb. 19, 2009, it was found that accumulated $gPr80^{env}$ which is always present in ts1-infected T-lineage cells, is apparently absent in ts1-GVT thymocytes. It was concluded that the low-ROS conditions in GVT-treated thymocytes, which can be brought about even without infection with ts1, could promote proper folding and normal cleavage of $gPr80^{env}$ into gp70 and PrP15E. To determine whether this might also be true in the intestines, Western blot of intestines from uninfected, ts1-only, and ts1-GVT mice were performed, stained with anti-gp70 to identify the molecular weights of gp70 immunoreactive proteins in the tissues. FIG. 6 shows that in the ts1-only intestine, gp70 immunoreactive material is present at both the 80 kDa (accumulated $gPr80^{env}$ and 70 kDa (processed gp70) positions in the gel. This two-band pattern is characteristic of gp70 Western blots of lysates from astrocytic cells infected in vitro. However, only gp70 was present in the intestinal lysate from the ts1-GVT mouse, and this was present in small amounts. The present invention provides that $gPr80^{env}$ is not accumulated in cells of the ts1-GVT intestine.

Like ts1, other cytopathic retroviruses, including HIV-1, SHIV and FIV, cause damage to the intestines and selective loss of CD4+ cells. Relevant to HIV-1 enteropathy, phthalazinediones including GVT therefore demonstrates efficiency in maintaining or resetting homeostasis by removing reactive oxygen species and thereby reducing oxidative stress caused by HIV-AIDS. Phthalazinediones as therapeutic agents, can prevent, maintain, or restore gut epithelial and T cell homeostasis in HIV-AIDS. This also suggests that repopulation of the intestines with autologous or transplanted bone marrow T-cell progenitors might be possible, even though HIV-infected cells are still present, even under HAART treatment.

Intestinal enterocytes normally stop expressing and releasing TSH when they have completed their differentiation and reached the CVJ. When pathogens infect the villus epithelium, however, TSH production is re-initiated in localized parts of the villus. Once the infection is cleared, the TSH-re-expressing epithelium is shed and replaced by TSH-cells. The same sequence of events, this time involving Ki67 expression, appears to accompany local and global infection, in the mouse gut. It has been shown that a proportion of all intestinal T cell subsets (CD4+ and CD8+ alike) express the TSHr. A local response loop involving the otherwise quiescent villus epithelium of the intestine may reactivate cell cycling and re-initiate TSH production, with TSH activating nearby T cells in the LP below, and the T cells, in turn, m the newly activated epithelium. If this were to occur on a large scale, and without limitation, continued infection/activation of LP T cells in the intestine could drive the shedding of the epithelium above, and could make this occur too fast for replacement. In turn, the activated epithelium, as long as it is present, could then send inappropriate signals to the LP T cells, maintaining their ectopic activation and thereby promoting their infection, and apoptosis. It appears that this sequence of events contributes to the collapse of the intestines after cytopathic retrovirus infection.

The results of these exemplary demonstrations presented here for ts1-GVT mice provide information in only one context, which is infection and treatment beginning at the same time (at birth) and continuing until all animals have died. This setting, however, has shown us that infection of intestinal cells with ts1 can coexist with apparent health in the intestines, both in the epithelial and LP lymphoid compartments. These conditions are accompanied by upregulation of Nrf2, and presumably of redox defenses in the epithelial cells, which may provide cysteine precursors and glutathione (GSH) to the LP T cells in amounts sufficient to allow their survival of ts1 infection. While not wishing to be bound by a specific theory, it is believed that if this occurs, it could also be responsible for the normal folding of Nrf2 in the ts1-GVT intestine, and this in turn would prevent all of the downstream consequences of $gPr80^{env}$ accumulation that lead to T cell apoptosis. GVT could also act as a chaperone, preventing misfolding of $gPr80^{env}$ or it could act as an antioxidant, detoxifying ROS as they appear in the infected cells.

The results shown here are significant in that they provide a new perspective regarding CD4+ cell loss in HIV-AIDS. ts1-infected mouse is a small-animal model for HIV-AIDS. Similarities between the two diseases have been identified in dozens of published papers from our laboratory and from others. Like HIV-1 in untreated human HIV-AIDS patients, ts1 is a savage enteropathic retrovirus in untreated mice. However, and remarkably, it has been shown herein that ts1 is harmless in the intestines of mice treated with GVT. Changes in CD4+ and CD8+ T cell subsets might be studied over time, for example, by fluorescence-activated cell sorting (FACS analysis) in both tissues. Preferably, this could be done at time points earlier than 30 dpi, because thymocyte/intestinal T cell numbers are so low at this time, and the thymus and villi are both collapsed, so that the processing of multiple animals for cells is likely to interfere with the quality of the results.

Under conventional HAART therapy regimens, the intestine can serve as a viral reservoir, allowing gastrointestinal symptoms to continue despite control of viral load in the blood. If GVT actually re-sets the redox tone in the ts1-infected mouse intestine, as it apparently does in the thymus, then repopulation of the intestine may be possible, either from autologous bone marrow or allogeneic bone marrow or stem cell grafting. In addition, GVT treatment may prove therapeutic for intestinal conditions that cause disease by initiating oxidative stress, in the epithelium or in the lymphoid cell compartments, because a more welcoming microenvironment is being maintained in the ts1-GVT intestines despite infection.

Example 2

Efficiency of GVT Treatment in Intestinal Infections

It has been demonstrated that TNF is responsible for granulocytes micro-biocidity increase, $H_2O_2$ production by neurophils, neurophil chemotaxis, granulocytes adhesion, t-killers formation, thymocyte proliferation, cell cytotocity, pro-coagular factor synthesis, thrombus growth on the surface of endothelia, increase synthesis of different acute-phase proteins, production of ACTH and prostaglandins. On the one hand, TNF is an important adaptation agent that increases organism resistance to infections by intensifying functional activity of neutrophilic granulocytes and macrophages. On the other hand, it imposes a direct cytotoxic influence on enterocysts and cells of connective tissue, by distorting lipids, inducing energetic exchange in tissues, oppressing ferment detoxication systems of both endogenous and exogenous toxins, causing microcirculatory distortions in irritation area. Accordingly, the major clinical symptoms in cases of acute intestinal infections (AII) are due to superfluous release of these compounds (nitric compounds) from hyperactivated macrophages. Therefore to remove the symptoms of pathologic process, it is necessary to reduce the level of these compounds.

GVT, on one hand, temporarily oppresses the hyperactivity of macrophages by reducing the TNF, which in turn provides rapid reduction of intoxication symptoms and therefore reduces oxidative stress. On the other hand GVT increases the activity of microbicide system of neurophilic granulocytes.

Clinical tests were performed on 56 patients suffering from acute intestine infections of different nature, accompanied by intoxication syndrome and diarrhea. All 56 patients had similar clinical manifestations, form and seriousness of the disease. The drug was prescribed to be used according to the following protocol: initial dose, 200 mg intramuscularly; then 3 hours later, a dose of 100 mg; and 3 hours later, a dose of 100 mg (400 mg per day). Treatment course for 54 patients was one day; for two patients the course was 36 hours.

In anamnesis of all patients no data of non-endurance or allergic reactions to any remedies was stated. GVT was administered to 54 patients within first hours after admission, before the application of traditional treatment methods, i.e., water-crystalloid solutions, vitamins, spasmolytics, as by acute dysentery and salmonellosis—antibacterial therapy.

Positive effect was observed within the first 24 hours in the group of patients being administered GVT. The majority of patients demonstrated a decrease in intoxication on the $1^{st}$ and $2^{nd}$ days. General weakness from different clinical manifestation disappeared on the $3^{rd}$ day. Even in patients admitted in the alter stages of the disease (i.e., on the $3^{rd}$ to $8^{th}$ day), general weakness, 4 to 6 days, was registered in only one patient with salmonellosis and one with acute dysentery. In the control group the weakness manifestations continued up to 4 to 6 days in 65% of patients.

Another clinical intoxication symptom in patients under study was body temperature increase. 19 patients had over 38 C/110 F fever. After GVT administration body temperature normalized on the $1^{st}$ or $2^{nd}$ day of treatment in 53 patients (94.6%).

Example 3

GVT Prevents HIV Induced Death of T Lymphoblastoid Cells in Association with Reduction of Intracellular ROS HIV-1 infection of cultured T lymphoblastoid cells (MT4) causes a dramatic increase in intracellular ROS, and this is associated with cell death. In HIV-infected cells treated with GVT (FIGS. 12 and 13), this increase in ROS does not occur, and the infected cells survive, although they continue to produce virus. This situation mirrors ts1 infection, in which ROS elevation causes death in T-lineage cells, while GVT prevents ROS elevation and inhibits ts1-mediated T cell death. Accordingly, lowering systemic redox in HIV-infected subjects, using phthalazinediones help to delay or prevent disease development.

Example 4

GVT Treatment of HIV Infected MT-4 Cells

GVT was added as a single dose on day 1 to uninfected MT-4 cells and had no effect on their viability. However when added to HIV-infected MT-4 cells at the same time, it protects the cells from HIV-induced killing for cells harvested at 3 or 4 dpi.

Figure 9:
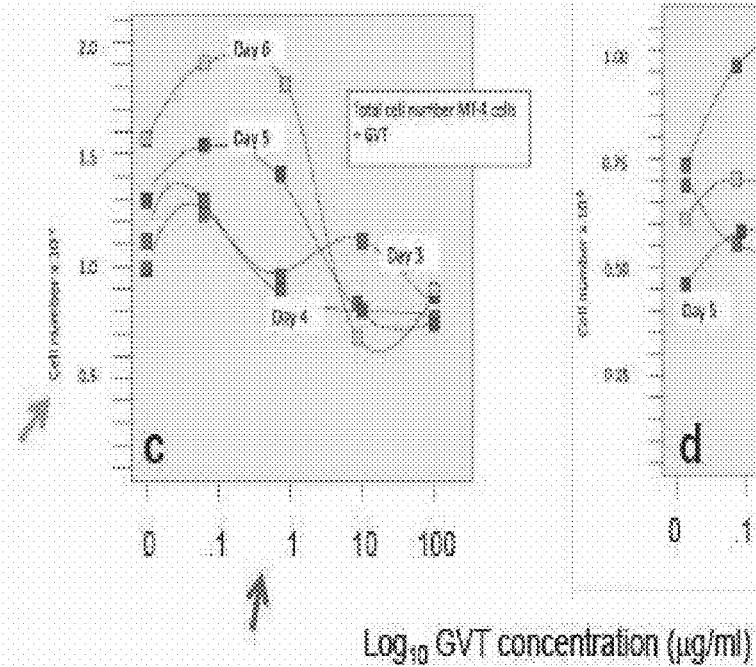
FIG. 9 is a diagram showing 3 dpi effects in GVT treated MT-4 cells in HIV infected subjects.
Figure 9:
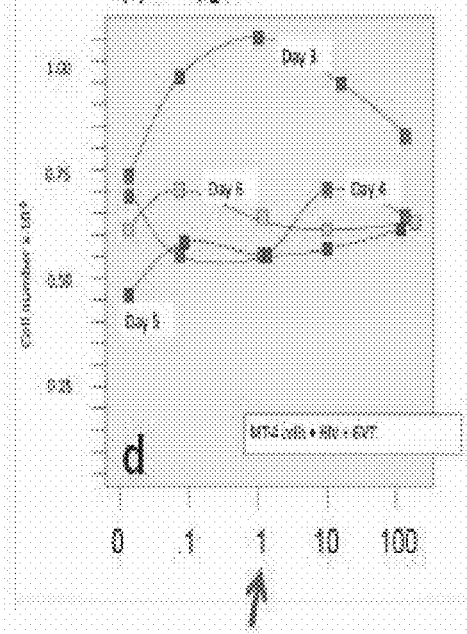
Figure 10:
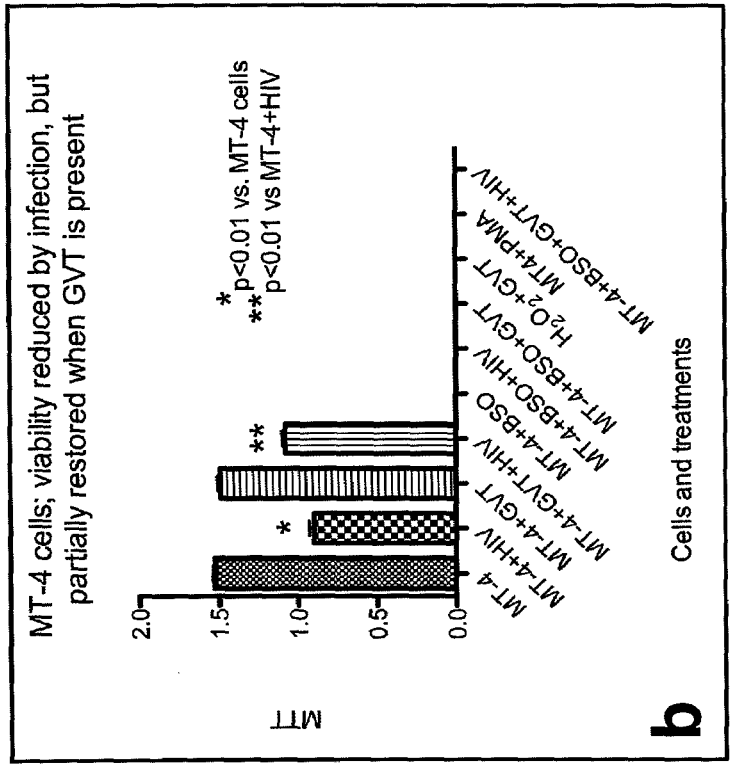
FIG. 10 is a diagram showing 6 dpi effects in GVT treated MT-4 cells in HIV infected subjects.
Figure 10:
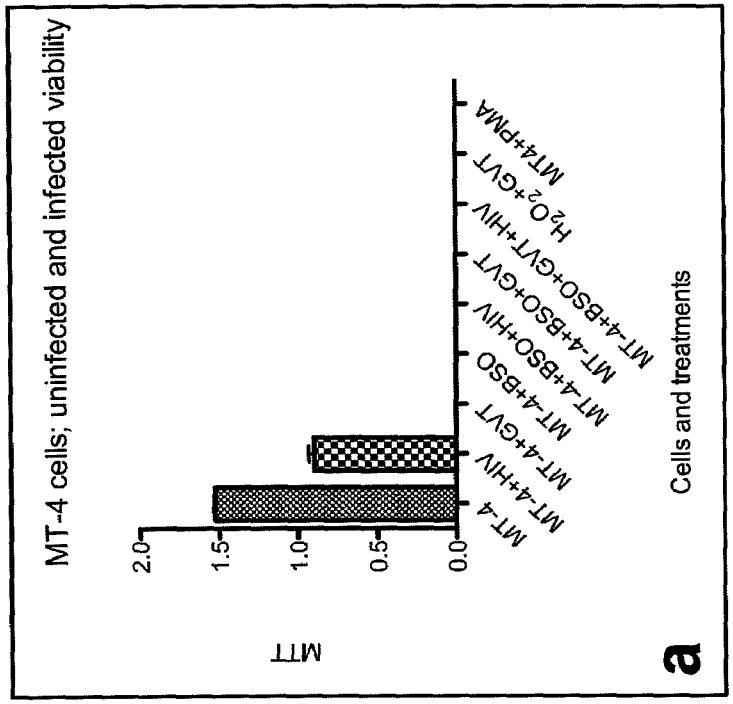

When added to uninfected MT-4 cells, GVT is mitogenic (see FIG. 9). When added as a single dose on day 1 to HIV-infected MT-4 cells, GVT is effective for protection in a dose-dependent fashion for cells harvested at 3 dpi. GVT was added to the cell culture every day for all six days of culture. HIV causes apoptosis of MT-4 cells, measurable when the cells are harvested at 6 dpi. GVT, added every day for the 6 days of culture, increases the viability of uninfected cells, and it significantly reduces apoptosis in the HIV-infected cells (see FIG. 10).

Figure 11:
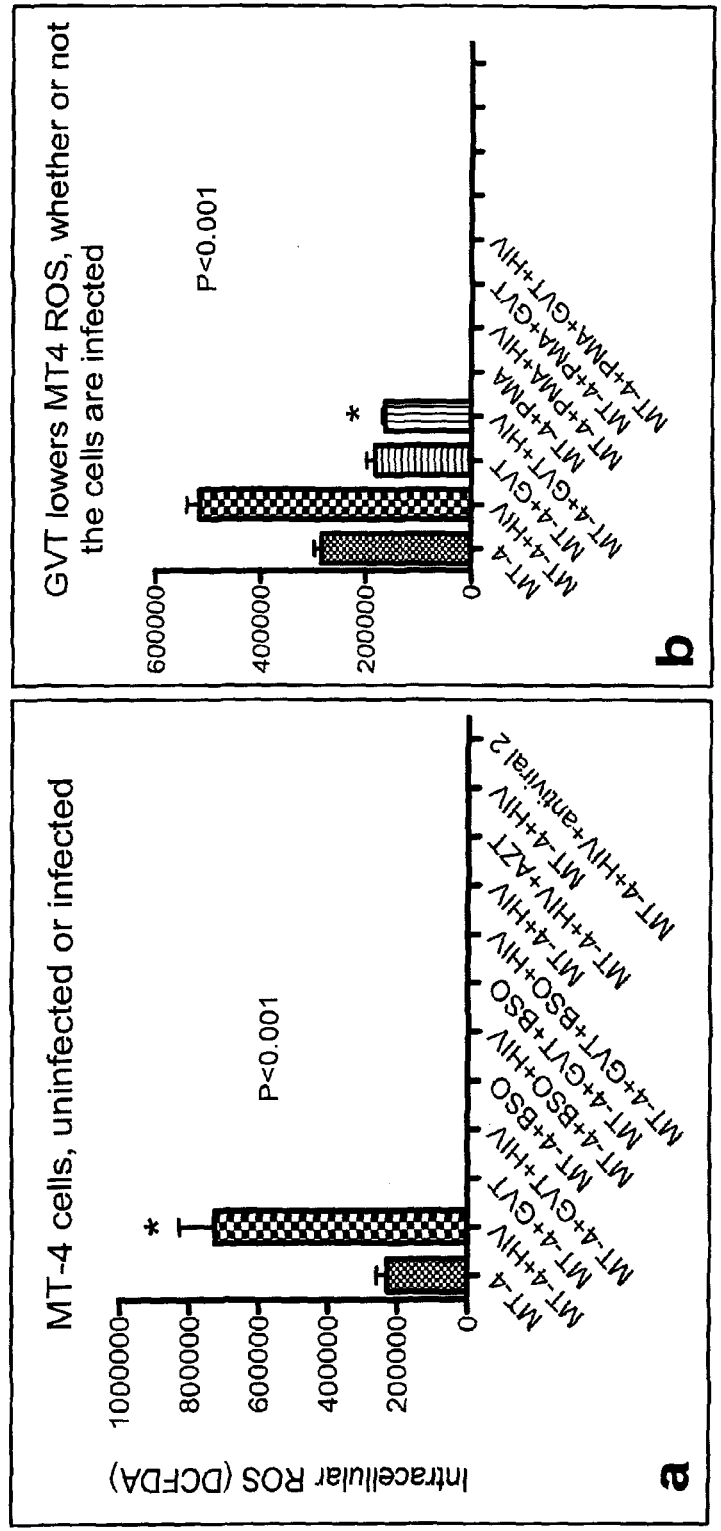
FIG. 11 is a diagram showing ROS production by HIV and the lowering effects of GVT.
Figure 12:
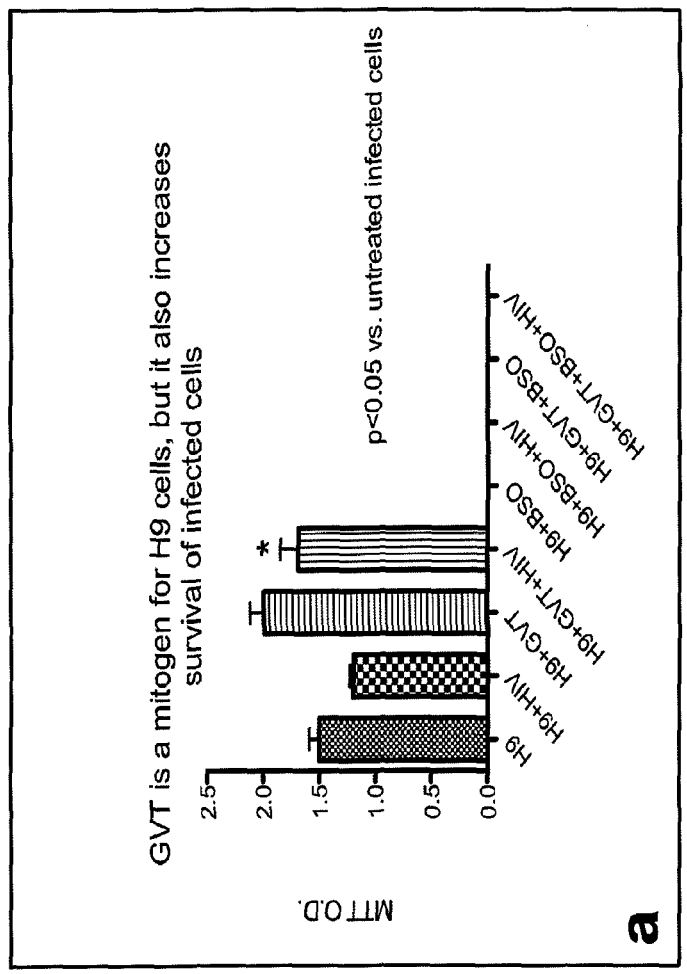
FIG. 12 is a diagram showing apoptosis of H9 cells and the effects of GVT treatment.

HIV infection causes ROS production in MT-4 cells (see FIG. 11). This is brought down in infected cells treated with GVT. A look at Nrf2 levels in the cells at days 1-6 dpi demonstrated an increase in cells treated with GVT, infected or not, and MT-4 survival associated with GVT treatment can be reduced by Nrf2 inhibition. In FIG. 12 it is demonstrated that HIV infection causes apoptosis of H9 cells. This is reduced significantly by GVT treatment. The dose-response curve for GVT in H9 cells is similar to that for MT-4 cells.

Figure 13:
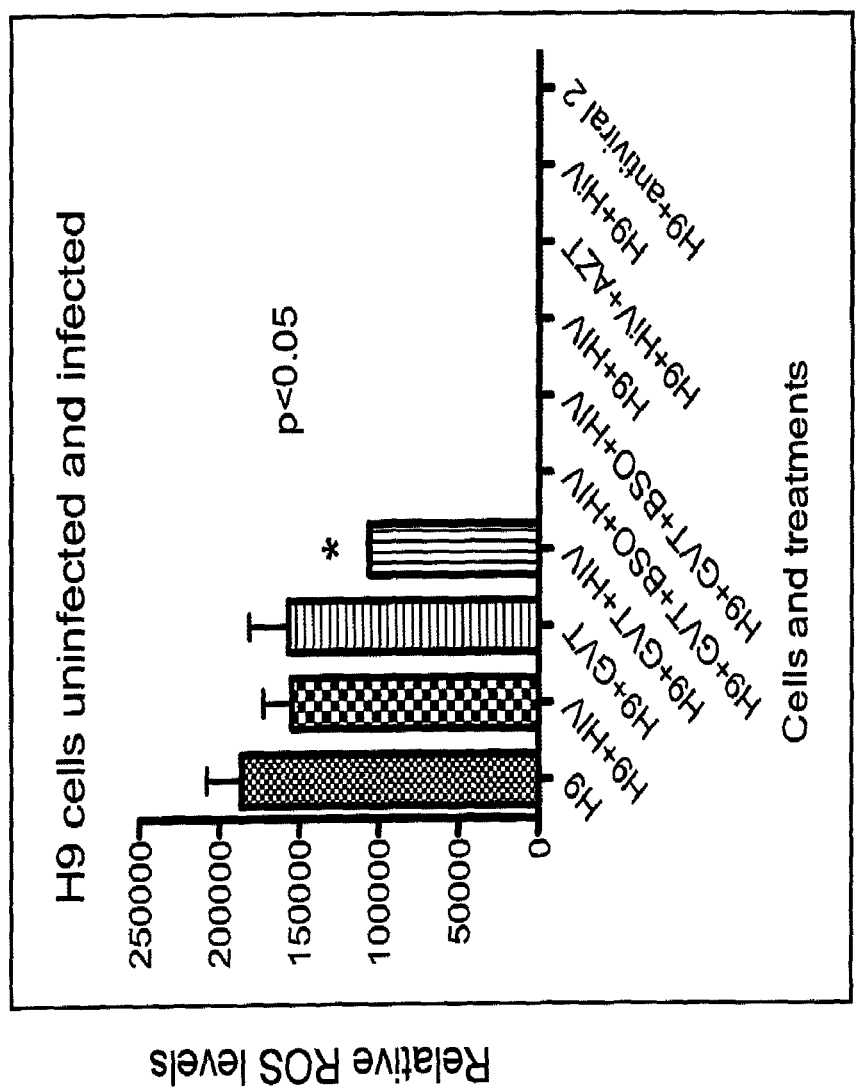
FIG. 13 is a diagram demonstrating that GVT significantly reduces apoptosis on HIV infected cells.

HIV infection does not significantly elevate ROS in H9 cells, and GVT does not dramatically reduce ROS in uninfected cells but GVT significantly reduces apoptosis of infected cells as demonstrated in FIG. 13.

Example 5

GVT Correction of ts1-Induced Dysregulation of Epithelial Organization

Figure 14:
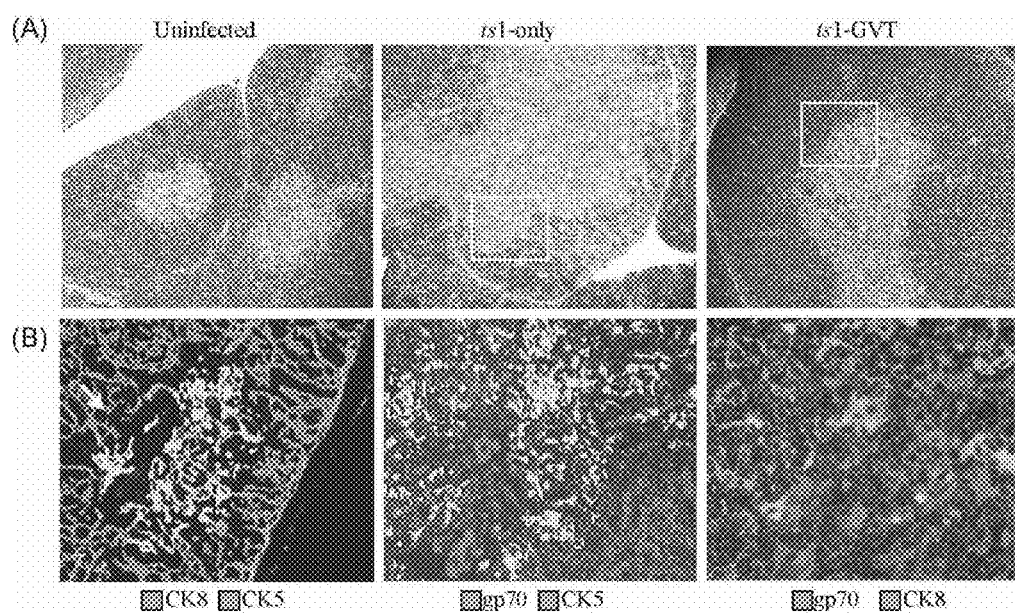
FIG. 14 is a diagram of corticomedullary epithelial organization and distribution of epithelial cell cytokeratins that are dysregulated at 30 dpi in ts1-only mice and mice treated with GVT.
Figure 15:
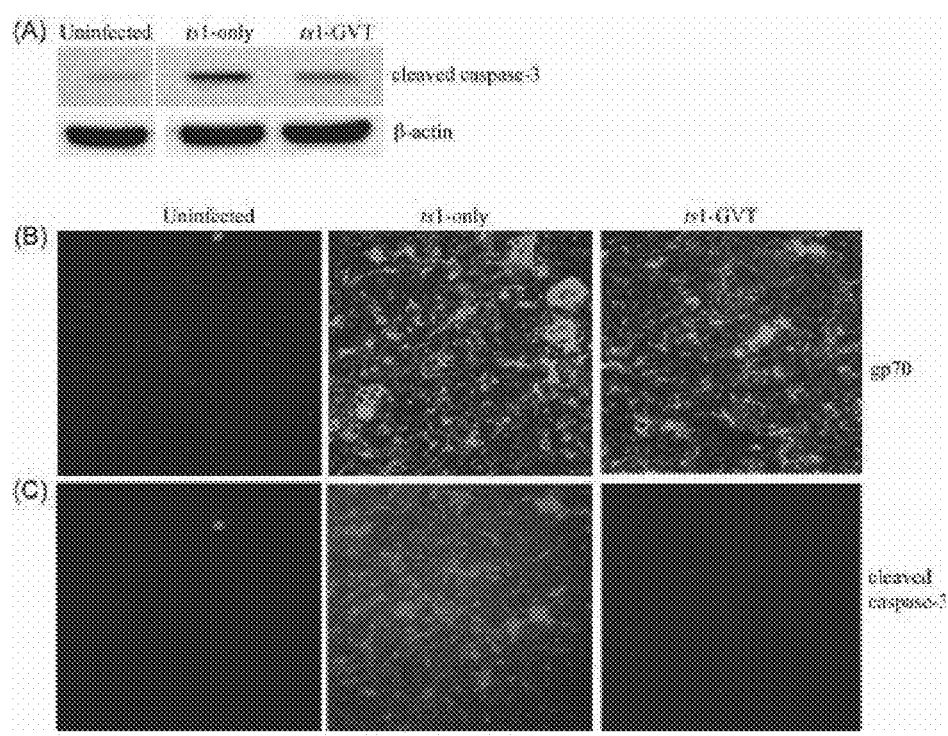
FIG. 15 is a diagram of cells of the thymus infected with ts1 and those subsequently treated with GVT.

In ts1-infected mice, as demonstrated by FIG. 14, corticomedullary epithelial organization and distribution of epithelial cell cytokeratins are dysregulated 30 dpi. Following GVT treatment, these disturbances are reduced. As demonstrated by FIG. 14 (A) showing the H&E stained sections of the thymi from uninfected, ts1-infected and ts1-GVT mice, the uninfected section shows one lobule whose cortex is dramatically thinned or absent, and whose medullary epithelium has spread out to occupy what otherwise would be cortical space. However, the ts1-GVT section shows normal corticomedullary organization in three lobules. The white boxes correspond to areas of the lobules in the immunostained panels below in par (B). As can be seen, the immunostained thymic lobule had normal corticomedullary and cytokeratin organization. The ts1-infected section contained gp70-positive and CK5-positive cells, all of which were infected. The medullary TECs appear to be expanding out of the medullary space, and also appeared to be infected. Treatment of the ts1-infected section with GVT contains large amounts of gp70-positive thymocyte profiles as well as many CK-positive but uninfected TECS, located generally behind a well-demarcated corticomedullary boundary (see FIG. 14 part (B)).

Example 6

GVT Prevents Cell Apoptosis in ts1-Infected Mice

In ts1-infected mice, cells of the thymus die by apoptosis. However, in treating these ts1-infected cells with GVT, apoptosis is prevented and the mice survive. As demonstrated in FIG. 15, part (A) shows a Western blot of thymocyte lysates for comparison of their contents of activated caspase-3. The ts1-infected thymocytes contain more of this enzyme than do uninfected thymocytes. However, upon treatment with GVT, the ts1-infected thymocyte only contained intermediate amounts of this enzyme. B-actin was used as a loading control. In parts (B and C) of FIG. 15, it was demonstrated that by sections of the thymi from the three groups identified above (ts1-infected, uninfected and ts1-infected but treated with GVT), stained for gp70 and for cleaved caspase-3. While both the ts1-infected and the GVT-treated sections contained gp70-positive infected cells, the cells treated with GVT did not have cells that were positive for cleaved caspase-3.

Example 7

GVT Reduces ROS Content in ts1-Infected Mice

As demonstrated in FIG. 16, ts1-infected mice have an abnormally high content of reactive oxygen species (ROS) in the thymocyte. Treatment with GVT was demonstrated to have reduced ROS, whether or not the cells were infected with ts1. The content of the ROS in the thymocyte is measured in terms of fluorescence units of DCFDA in lysates of thymocytes infected with ts1, uninfected and those treated with GVT.

Example 8

GVT Prevents Accumulation of gPr80$^{env}$ in ts1-Infected Mice

Figure 17:
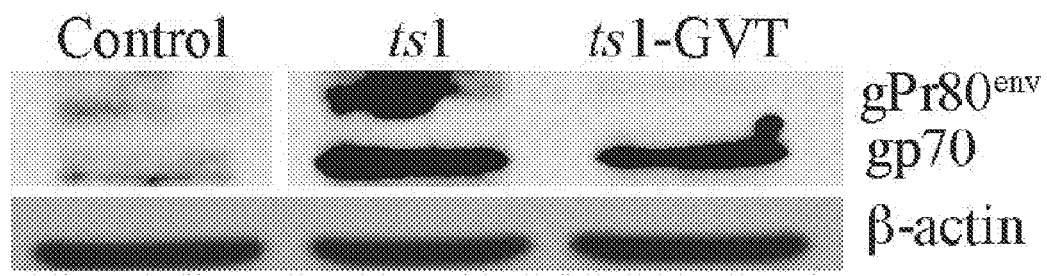
FIG. 17 is a diagram of a Western blot of 30 dpi thymic tissues from uninfected, ts1-only and ts1-GVT mice.
Figure 18:
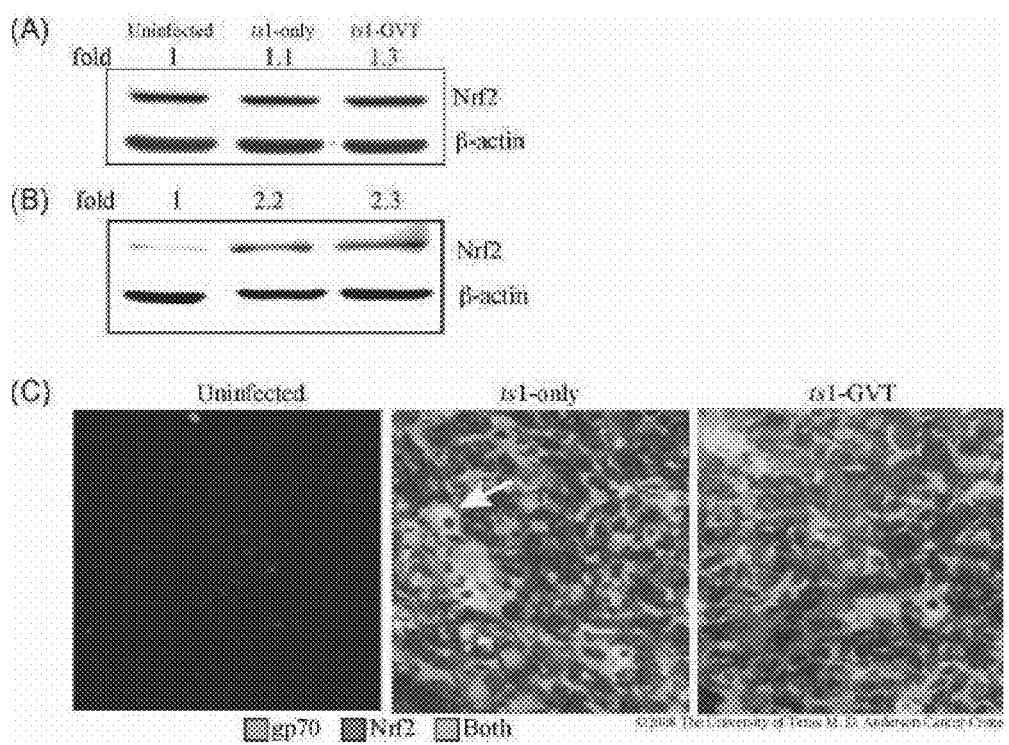
FIG. 18 is a diagram of levels of the transcription factor Nrf2 in ts1-only and ts1-GVT mice.

Western blot of 30 dpi thymic tissues from uninfected, ts1-infected and GVT treated mice, are presented in FIG. 17. gPr80env is a viral preprotein. The antibody identifies epitopes present in both the band present at 80 kDa, which is gPr80env, and in the band at the 70 kDa position (gp70). This blot shows that gPr80env accumulation occurred in this ts1-only thymus, but not in the thymic tissues of the mice tissues treated with GVT after ts1 infection. Some GVT treated thymi contained gPr80env at 30 dpi, but in significantly smaller amounts than those seen for thymi of ts1-only mice, and with a correspondingly larger gp70 band, than those seen for ts1-only thymi.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

[1] Asjo B, Fenyo E M, Klein G. Moloney virus (M-MuLV) leukemogenesis: Virus spread, antibody production and antigenic expression in neonatally virus-inoculated young mice. mt J Cancer 1981; 28:65-70.

[2] Wong P K, McCarter J A. Genetic studies of temperature-sensitive mutants of Moloney murine leukemia virus. Virology 1973; 53:319-326.

[3] Kamps C A, Lin Y-C, Wong P K Y. Oligomerization and transport of the envelope protein of Moloney murine leukemia virus-TB and of ts1, a neurovirulent temperature sensitive mutant of MoMuLV-TB. Virology 1991; 184:687-694.

[4] Szurek P F, Yuen P H, Ball J K, Wong P K. A Val-25-to-Ile substitution in the envelope precursor polyprotein, gPr8O$^{env}$, is responsible for the temperature sensitivity, inefficient processing of gPr8Oenv, and neurovirulence of ts1, a mutant of Moloney murine leukemia virus TB. J Virol 1990; 64:467-475.

[5] Wong P K, Szurek P F, Floyd E, Saha K, Brooks B R. Alteration from T- to B-cell tropism reduces thymic atrophy and cytocidal effects in thymocytes but not neurovirulence induced by ts1, a mutant of Moloney murine leukemia virus TB. Proc Natl Acad Sci USA 1991; 88:8991-8995.

[6] Wong P K Y, Lynn W S, Lin Y C, Choe W, Yuen P H. ts1-MoMuLV: a murine model of neuroimmunodegeneration. Neuroimmunodegeneration. 1998: 75-93.

[7] Kim H T, Qiang W, Wong P K, Stoica G. Enhanced proteolysis of IKBU and 1KB 13 proteins in astrocytes by Moloney murine leukemia virus (MoMuLV)-ts1 infection: a potential mechanism of NF-KB activation. J Neurovirol 2001; 7:466-475.

[8] Jiang Y, Scofield V L, Yan M, Qiang W, Liu N, Reid A J, et al. Retrovirus-induced oxidative stress with neuroimmunodegeneration is suppressed by antioxidant treatment with a refined monosodium a-luminol (Galavit). J Virol 2006; 80:4557-4569.

[9] Kim H T, Tasca S, Qiang W, Wong P K, Stoica G. Induction of p53 accumulation by Moloney murine leukemia virus-ts I infection in astrocytes via activation of extracellular signal-regulated kinases 1/2. Lab Invest 2002; 82:693-702.

[10] Kim H T, Waters K, Stoica G, Qiang W, Liu N, Scofield V L, et al. Activation of endoplasmic reticulum stress signaling pathway is associated with neuronal degeneration in MoMuLV-ts1-induced spongiform encephalomyelopathy. Lab Invest 2004; 84:816-827.

[11] Kim H T, Qiang W, Liu N, Scofield V L, Wong P K, Stoica G. Up-regulation of astrocyte cyclooxygenase-2, CCAAT/enhancer-binding protein-homology protein, glucose-related protein 78, eukaryotic initiation factor 2a, and c-Jun N-terminal kinase by a neurovirulent murine retrovirus. J Neurovirol 2005; 11:166-179.

[12] Liu N, Qiang W, Kuang X, Thuillier P. Lynn W S, Wong P K. The peroxisome proliferator phenylbutyric acid (PB A) protects astrocytes from ts 1 MoMuLV-induced oxidative cell death. J Neurovirol 2002; 8:318-325.

[13] Liu N, Kuang X, Kim H T, Stoica G, Qiang W, Scofield V L, et al. Possible involvement of both endoplasmic reticulum- and mitochondria-dependent pathways in MoMuLV-ts1 induced apoptosis in astrocytes. J Neurovirol 2004; 10:189-198.

[14] Liu N, Scofield V L, Qiang W, Yan M, Kuang X, Wong P K. Interaction between endoplasmic reticulum stress and caspase 8 activation in retrovirus MoMuLV-ts1 infected astrocytes. Virology 2006; 348:398-405.

[15] Qiang W, Cahill J M, Liu J, Kuang X, Liu N, Scofield V L, et al. Activation of transcription factor Nrf-2 and its downstream targets in response to Moloney murine leukemia virus ts1-induced thiol depletion and oxidative stress in astrocytes. J Virol 2004; 78:i 1926-i 1938.

[16] Qiang W, Kuang X, Liu J. Liu N, Scofield V. Stoica G, et al. Astrocytes survive chronic infection and cytopathic effects of the ts 1 mutant of the retrovirus Moloney murine leukemia virus by upregulation of antioxidant defenses. J Virol 2006; 80:3273-3284.

[17] Zhang M, Thurig S. Tsirigotis M, Wong P K, Reuhi K R, Gray D A. Effects of mutant ubiquitin on ts1 retrovirus-mediated neuropathology. J Virol 2003; 77:7193-7201.

[18] Clase A C, Dimcheff D E, Favara C, Dorward D, McAtee F J, Parrie L E, et al. Oligodendrocytes are a major target of the toxicity of spongiogenic murine retroviruses. Am J Pathol 2006; 169:1026-1038.

[19] Wong P K Y, Lynn W S, Lin Y C, Choe W, Yuen P H. ts1-MoMuLV: a murine model of neuroimmunodegeneration. In: Wong P K Y, Lynn W S, editors. Neuroimmunodegeneration. Berlin: Springer, 1998; 75-93.

[20] Clark S, Duggan J, Chakraborty J. ts1 and LP-BM5: a comparison of two murine retrovirus models for HIV. Viral Immunol 2001; 14:95-109.

[21] Sankaran S, George M D, Reay E, Guadalupe M, Flarnm J, Prindiville T, et a!. Rapid onset of intestinal epithelial barrier dysfunction in primary human immunodeficiency virus infection is driven by an imbalance between immune response and mucosal repair and regeneration. J Virol 2008; 82:538-545.

[22] Veazey R S, Tham I C, Mansfield K G, DeMaria M, Forand A E, Shvetz D E, et al. Identifying the target cell in primary simian immunodeficiency virus (SW) infection: Highly activated memory CD4+ T cells are rapidly eliminated in early SW infection in vivo. J Virol 2000; 74:57-64.

[23] Fukazawa Y, Miyake A, Ibuki K, Inaba K, Saito N, Motohara M, et al. Small intestine CD4+ T cells are profoundly depleted during acute simian-human immunodeficiency virus infection, regardless of viral pathogenicity. J Virol 2008; 82: 6039-6044.

[24] Howard K E, Burkhard M J. Fly infection induces unique changes in phenotype and cellularity in the medial iliac lymph node and intestinal IEL. AIDS Res Hum Retroviruses 2007; 23:720-728.

[25] Ishikawa H, Saito H, Suzuki K, Oida T, Kanamori Y. New gut associated lymphoid tissue "cryptopatches" breed murine intestinal intraepithelial T cell precursors. Immunol Res 1999; 20:243-250.

[26] Potten C S, Martin K, Kirkwood T B. Ageing of murine small intestinal stem cells. Novartis Found Symp 2001; 235:66-79; discussion 79-84, 101-104.

[27] Barker N, van de Wetering M, Clevers H. The intestinal stem cell. Genes Dev 2008; 22:1856-64.

[28] van der Flier L G, Clevers H. Stem cells, self-renewal, and differentiation in the intestinal epithelium. Annu Rev Physiol 2008, epub ahead of print.

[29] Guy-Grand D, Azogui 0, Celli 5, Darche S, Nussenzweig M C, Kourilsky P, et al. Extrathymic T cell lymphopoiesis: ontogeny and contribution to gut intraepithelial lymphocytes in athymic and euthymic mice. J Exp Med 2003; 197:333-341.

[30] Ishikawa H, Naito T, Iwanaga T, Takahashi-Iwanaga H, Suematsu M, Hibi T, et al. Curriculum vitae of intestinal intraepithelial T cells: their developmental and behavioral characteristics. Immunol Rev 2007; 215:154-165.

[31] Klein J R. Thymus-independent development of gut T cells. Chem Immunol 1998; 71:88-102.

[32] Lambolez F, Azogui 0, Joret A M, Garcia C, von Boehmer H, Di Santo J, et al. Characterization of T cell differentiation in the murine gut. J Exp Med 2002; 195:437-49.

[33] Podd B S, Thoits J, Whitley N, Cheng H Y, Kudla K L, Taniguchi H, et al. T cells in cryptopatch aggregates share TCR y variable region junctional sequences with y T cells in the small intestinal epithelium of mice. J Immunol 2006; 176:6532-6542.

[34] Cheroutre H, Lambolez F. The thymus chapter in the life of gut-specific ultra epithelial lymphocytes. CUIT Opin Immunol 2008; 20: 185-191.

[35] Klug D B, Crouch E, Carter C, Coghian L, Conti C J, Richie E R. Transgenic expression of cyclin D1 in thymic epithelial precursors promotes epithelial and T cell development. J Immunol 2000; 164:1881-1888.

[36] Wang J, Whetsell M, Klein J R. Local hormone networks and intestinal T cell homeostasis. Science 1997; 275:1937-1939.

[37] Scofield V L, Montufar-Solis D, Cheng E, Estes M K, Klein J R. Intestinal TSH production is localized in crypt enterocytes and in villus 'hotblocks' and is coupled to IL 7 production: evidence for involvement of TSH during acute enteric virus infection. Immunol Lett 2005; 99:36-44.

[38] Shanahan F. A gut reaction: lymphoepithelial communication in the intestine. Science 1997; 275:1897-1898.

[39] Montufar-Solis D, Garza T, Teng B B, Klein J R. Upregulation of ICOS on CD43+ CD4+ murine small intestinal intraepithelial lymphocytes during acute reovirus infection. Biochem Biophys Res Commun 2006; 342:782-790.

[40] Pazos-Moura C C. Ortiga-Carvalho T M, Gaspar de Moura E. The autocrine/paracrine regulation of thyrotropin secretion. Thyroid 2003; 13:167-175.

[41] MacDonald T T. Epithelial proliferation in response to gastrointestinal inflammation. Ann NY Acad Sci 1992; 664:202-209.

[42] Polyak K, Hamilton S R, Vogelstein B, Kinzler K W. Early alteration of cell cycleregulated gene expression in colorectal neoplasia. Am J Pathol 1996; 149:381-387.

[43] Moi P, Chan K, Asunis I, Cao A, Kan Y W. Isolation of NF-E2-related factor 2 (Nrf2), a NF-E2-like basic leucine zipper transcriptional activator that binds to the tandem NFE2/AP1 repeat of the 3-globin locus control region. Proc Nati Acad Sci USA 1994; 91:9926-9930.

[44] Chen X L, Kunsch C. Induction of cytoprotective genes through Nrf2/antioxidant response element pathway: a new therapeutic approach for the treatment of inflammatory diseases. Cun Pharm Des 2004; 10:879-891.

[45] Nguyen T, Yang C S, Pickett C B. The pathways and molecular mechanisms regulating Nrf2 activation in response to chemical stress. Free Radic Biol Med 2004; 37:433-441.

[46] Gharavi N, Haggarty 5, El-Kadi A O. Chemoprotective and carcinogenic effects of tertbutylhydroquinone and its metabolites. CulT Drug Metab 2007; 8: 1-7.

[47] Purdom-Dickinson S E, Sheveleva E V, Sun H, Chen Q M. Translational control of Nrf2 protein in activation of antioxidant response by oxidants. Mo! Pharmacol 2007; 72:10741081.

[48] Walsh J G, Cullen S P, Sheridan C, Luthi A U, Gerner C, Martin S J. Executioner caspase-3 and caspase-7 are functionally distinct proteases. Proc Nati Acad Sci USA 2008; 105: 12815-12819.

[49] Lau A, Vi!leneuve N F, Sun Z, Wong P K, Zhang D D. Dual roles of Nrf2 in cancer. Pharmacol Res 2008.

[50] Belmonte L, Olmos M, Fanin A, Parodi C, Bare P. Concetti H, et al. The intestinal mucosa as a reservoir of HIV-1 infection after successful HAART. AIDS 2007; 21:21062108.

[51] Bengmark 5, Jeppson B. Gastrointestinal surface protection and mucosa reconditioning. J Parenter Enteral Nutr 1995; 19:410-415.

[52] Schmidt W, Wahschaffe U, Schafer M, Zippel T, Arvand M, Meyerhans A, et al. Rapid increase of mucosal CD4 T cells followed by clearance of intestinal cryptosporidiosis in All references cited herein are incorporated by reference in their entirety.

The invention claimed is:

1. A method of treating glaucoma in a subject comprising; administering a therapeutically effective amount of 5-amino-2,3-dihydrophthalazine-1,4-dione to the subject having an intestinal environment with an imbalanced redox state such that the oxidative stress related to the glaucoma is modulated.

2. The method of claim 1, wherein the phthalazinedione is administered with a compound selected from the group consisting of a glutathione, cysteine, lipoic acid, biopterin, hydralazine, rasagiline, thioredoxin, ferulic acid, minocycline, menadione, tetracycline, isosorbate dinitrate, dextromethorphan, dithiothreitol, carnosine, and clomethiazole, wherein the metabolic distress is not caused by a disease of cellular senescence.

3. The method of claim 1, wherein the 5-amino-2,3-dihydrophthalazine-1,4-dione is in a therapeutically effective form selected from the group consisting of tablet, capsule, granule, powder, solution suspension, microsphere, liposome, colloid, spray and suppository.

4. The method of claim 1, wherein the 5-amino-2,3-dihydrophthalazine-1,4-dione is administered by a means selected from the group consisting of intravenous, intramuscular, intraperitoneal, subcutaneous, oral, nasal, mucosal, transdermal, parenteral, vaginal, and rectal.

5. The method of claim 1, wherein the 5-amino-2,3-dihydrophthalazine-1,4-dione is administered in combination with a standard therapy selected from the group consisting of surgery, drug therapy, and nutrition.

6. The method of claim 1, wherein the phthalazinedione is administered in an amount of about 0.01 mg/kg to about 100.0 mg/kg of body weight.

7. The method of claim 1, wherein the phthalazinedione is administered in an amount of about 1.0 mg per day to about 10,000.0 mg per day.

8. A method of treating glaucoma in a subject infected with HIV-AIDS comprising; administering a therapeutically effective amount of 5-amino-2,3-dihydrophthalazine-1,4-dione to the subject having an intestinal environment with an imbalanced redox state such that the oxidative stress related to the glaucoma is modulated.

9. The method of claim 8, wherein the 5-amino-2,3-dihydrophthalazine-1,4-dione is in a therapeutically effective form selected from the group consisting of tablet, capsule, granule, powder, solution suspension, microsphere, liposome, colloid, spray and suppository.

10. The method of claim 8, wherein the 5-amino-2,3-dihydrophthalazine-1,4-dione is administered by a means selected from the group consisting of intravenous, intramuscular, intraperitoneal, subcutaneous, oral, nasal, mucosal, transdermal, parenteral, vaginal, and rectal.

11. The method of claim 8, wherein the 5-amino-2,3-dihydrophthalazine-1,4-dione is administered in combination with a standard therapy selected from the group consisting of surgery, drug therapy, and nutrition.

12. The method of claim 1, wherein the phthalazinedione is administered in an amount of about 0.01 mg/kg to about 100.0 mg/kg of body weight.

13. The method of claim 1, wherein the phthalazinedione is administered in an amount of about 1.0 mg per day to about 10,000.0 mg per day.

* * * * *